United States Patent
Lynd et al.

(10) Patent No.: US 10,533,194 B2
(45) Date of Patent: Jan. 14, 2020

(54) SYSTEMS AND METHODS FOR ENHANCING MICROBIAL CONVERSION OF BIOMASS USING MECHANICAL AUGMENTATION

(71) Applicant: The Trustees of Dartmouth College, Hanover, NH (US)

(72) Inventors: Lee R. Lynd, Meriden, NH (US); Julie M. D. Paye, Randolph Center, VT (US); Michael Balch, Etna, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

(21) Appl. No.: 14/968,765

(22) Filed: Dec. 14, 2015

(65) Prior Publication Data
US 2016/0168596 A1    Jun. 16, 2016

Related U.S. Application Data

(63) Continuation-in-part of application No. PCT/US2014/042432, filed on Jun. 14, 2014.

(60) Provisional application No. 61/835,447, filed on Jun. 14, 2013, provisional application No. 62/197,237, filed on Jul. 27, 2015, provisional application No. 62/153,327, filed on Apr. 27, 2015.

(51) Int. Cl.
| | |
|---|---|
| *C12P 7/10* | (2006.01) |
| *C12M 1/33* | (2006.01) |
| *C12P 7/06* | (2006.01) |
| *C12R 1/145* | (2006.01) |
| *C12M 1/00* | (2006.01) |

(52) U.S. Cl.
CPC ............ *C12P 7/10* (2013.01); *C12M 45/02* (2013.01); *C12P 7/06* (2013.01); *C12P 7/065* (2013.01); *C12R 1/145* (2013.01); *C12M 21/12* (2013.01)

(58) Field of Classification Search
None
See application file for complete search history.

(56) References Cited

U.S. PATENT DOCUMENTS

| | | | | |
|---|---|---|---|---|
| 4,338,399 A | * | 7/1982 | Weil ...................... | C13K 1/04 435/105 |
| 2011/0143412 A1 | | 6/2011 | Kim et al. | |
| 2012/0028325 A1 | | 2/2012 | Herring et al. | |

FOREIGN PATENT DOCUMENTS

| | | |
|---|---|---|
| WO | WO 2010/073083 A2 | 7/2010 |
| WO | WO 2010/073083 A3 | 7/2010 |
| WO | WO 2012/083244 A2 | 6/2012 |
| WO | WO 2012/083244 A3 | 6/2012 |

OTHER PUBLICATIONS

International Search Report and Written Opinion in PCT/US2014/042432 dated Nov. 4, 2014, 7 pp.

(Continued)

*Primary Examiner* — Allison M Fox
*Assistant Examiner* — Qing Xu
(74) *Attorney, Agent, or Firm* — Lathrop Gage LLP

(57) ABSTRACT

A system and method for converting biomass with no chemical pretreatment is disclosed. Combination of a microbial system and the use of mechanical disruption during fermentation may help achieve high conversion rate without the extra cost and undesirable by-products typically associated with the pretreatment process.

9 Claims, 17 Drawing Sheets

(56) References Cited

OTHER PUBLICATIONS

Archambault-Leger et al. "Integrated analysis of hydrothermal flow through pretreatment," Biotechnology for Biofuels, Jul. 19, 2012 (Jul. 19, 2012) vol. 5, No. 49, 10 pp.
Detroy et al. "Biomass conversion; fermentation chemicals and fuels," Critical Reviews in 3, 14, Microbiology, Feb. 1983 (Feb. 1983), vol. 10, Issue 3, 26 pp.
Extended European Search Report dated Dec. 21, 2016 for European Patent Application No. 14810426.8 (13 pages).
Neilson et al: "Enhancement of enzymatic hydrolysis by simultaneous attrition of cellulosic substrates", Biotechnology and Bioengineering., vol. 24, No. 2, Feb. 1982 (Feb. 1982) pp. 293-304.
International Preliminary Report on Patentability dated Dec. 15, 2015, for International Patent Application No. PCT/US2014/042432 (6 pages).
European Patent Application No. 14810426.8; Communication pursuant to Article 94(3) EPC dated Jun. 11, 2018; 11 pgs.
Chinese Patent Application No. 201480045364.X, English translation of Office Action dated Sep. 26, 2018, 12 pages.
Chinese Patent Application No. 201480045364.X, English translation of Office Action dated Apr. 23, 2019, 9 pages.

\* cited by examiner

SYSTEMS AND METHODS FOR ENHANCING MICROBIAL CONVERSION OF BIOMASS USING MECHANICAL AUGMENTATION

RELATED APPLICATIONS

This application is a continuation-in-part and claims priority to PCT application PCT/US14/42432 filed Jun. 14, 2014, which claims priority to U.S. Patent application 61/835,447 filed Jun. 14, 2013. This application also claims priority to U.S. Patent application 62/153,327 filed Apr. 27, 2015, and U.S. Patent application 62/197,237 filed Jul. 27, 2015. The entire content of all of the above-identified applications are hereby incorporated by reference into this application.

U.S. GOVERNMENT RIGHTS

This invention was made with Government support under Grant No. DE-AC05-00OR22725, awarded by the U.S. Department of Energy. The Government has certain rights in this invention.

BACKGROUND

I. Field of the Invention

The disclosure relates to conversion of insoluble cellulosic biomass to biofuel or other useful products. More particularly, the disclosure pertains to the use of microorganisms and mechanical disruption to enhance cellulosic biomass solubilization and conversion.

II. Description of the Related Art

Cellulosic biomass is a relatively inexpensive, renewable and abundant material that can be used to generate fuels, chemicals, fibers, and energy. However, large-scale utilization of plant biomass is hindered, at least in part, by the lack of low-cost technologies capable of efficiently converting the biomass into soluble, reactive intermediates—notably including sugars. For example, most plant cell walls are resistant to digestion by cellulase enzymes.

Pretreatment of biomass may render the biomass more amenable to enzymatic digestion. Pretreatment may remove biomass components such as lignin and/or hemicellulose that impede access to cellulase enzymes. Pretreatment may also cause structural changes (e.g. particle size, porosity, surface area) in the biomass. Various biomass pretreatment technologies have been developed. Examples of these developments include use of dilute acids or bases, steam explosion, autohydrolyisis, controlled pH, AFEX, and aqueous ammonia pretreatment.

It is commonly believed that pretreatment of cellulosic biomass is required for biological conversion of cellulosic biomass. According to this common belief, pretreatment using high temperature and/or chemicals is necessary prior to biological processing in order to achieve the high solubilization yields upon subsequent biological processing that are generally required for economic viability.

However, capital and operating costs for pretreatment are substantial, and pretreatment further increases processing costs by negatively impacting the performance of downstream processing operations. In particular, all known pretreatments either produce compounds which inhibit hydrolysis and fermentation or require recovery of chemical reagents (for example, ammonia or ionic liquids), or both.

It is also believed that milling requires too much energy to be practical as a pretreatment prior to solubilization using fungal cellulase. It is disclosed here that (a) certain anaerobic cellulolytic microbes such as *Clostridium thermocellum* are capable of achieving significant solubilization of lignocellulose without pretreatment, (b) the resistance of such microbes to mechanical disruption, and (c) it is possible and beneficial to enhance solubilization by mechanical disruption of partially-solubilized solids—and in particular during microbial fermentation—termed co-treatment.

SUMMARY

The presently disclosed instrumentalities advance the art by providing systems and methods for converting cellulosic biomass more efficiently. In one embodiment, higher extents and rates of cellulosic feedstock solubilization may be achieved with little or no pretreatment by using cellulolytic microbes in conjunction with mechanical disruption of lignocellulose particles during the conversion process.

In one embodiment, a new approach is disclosed to enhance conversion of lignocellulosic biomass by applying mechanical disruption (e.g. by milling). In another embodiment, it is disclosed that mechanical disruption of partially-fermented biomass material is more effective than mechanical attack of unreacted material (i.e., before fermentation has been initiated). In another embodiment, mechanical disruption is commenced after biological processing has been initiated, and hence the mechanical disruption is acting on partially reacted solids (or partially solubilized biomass).

The combination of microbial cellulose fermentation with mechanical disruption of partially solubilized lignocellulose particles has not been shown for the production of fuels or chemicals from cellulosic biomass. Most, if not all commercial processes for biological conversion of cellulosic biomass to ethanol or other fuels/chemicals use added cellulase (typically in a purified form) and require a thermo/chemical pretreatment step, both of which add significant cost to the process. The presently disclosed process may eliminate the requirements of both added cellulase and pretreatment.

In one embodiment, a novel process involving mechanical attack of lignocellulose during microbial conversion of liquid biofuel production is disclosed. In one aspect, anaerobic cellulolytic bacteria are shown to be highly effective at solubilizing lignocellulose, as compared to industry standard fungal cellulase. In another aspect, yeast cells are generally known to be resistant to inhibition by certain chemicals (e.g. those added for or arising from pretreatment) but they may be sensitive to mechanical attack. By contrast, bacteria are shown to be resistant to mechanical attack. More specifically, it is shown here that *Clostridium thermocellum* is insensitive to mechanical attack at intensities sufficient to markedly increase solubilization whereas yeast is highly sensitive at the same intensities.

In another embodiment of this disclosure, mechanical attack may be employed in conjunction with the use of cellulolytic bacteria. In one aspect, no chemical attack is used. In another aspect, mechanical attack may be carried out during fermentation acting on partially reacted material. In another embodiment, it is shown here that mechanical attack during fermentation is more effective than mechanical attack of unreacted material (i.e., before fermentation has been initiated). In another embodiment, mechanical disruption is more effective on partially solubilized biomass material as compared to mechanical disruption on unsolubilized material. In addition, mechanical disruption on partially solubilized biomass also requires less energy consumption as compared to energy consumption required for mechanical disruption on unsolubilized material. In another embodiment, "partially solubilized" may mean that at least about 10%, at least about 20%, at least about 30%, at least about 40%, at least about 50%, at least about 60%, at least about 70%, at least about 80%, or at least about 90% of the biomass material has been solubilized.

In one embodiment, the disclosed system may contain a biomass comprising lignocellulosic particles, a reactor for holding the biomass, a microorganism capable of mediating solubilization of biomass particles and fermenting resultant sugars to desired products, and means for mechanically disrupting the lignocellulosic particles. In another embodiment, the system may be configured such that the biomass is simultaneously or intermittently subject to both mechanical disruption by the disrupting means and fermentation without reinoculation following mechanical disruption and fermentation by the microorganism for a substantial period of time. The term "substantial period of time" refers to a period of time within which significant disruption or fermentation has occurred on the biomass. In one aspect, the biomass has not been pretreated before being exposed to the disruption or fermentation. In another aspect, the biomass is not pretreated with any chemicals. In another aspect, the biomass has been heat sterilized before being loaded into the reactor. In another aspect, the reactor is a closed reactor.

In one embodiment, the system may be configured such that the biomass is subject to mechanical disruption after the biomass is partially solubilized. In another embodiment, the biomass may be continuously subject to mechanical disruption and fermentation at the same time. In another embodiment, mechanical disruption is applied intermittently. In another embodiment, no reinoculation of the microorganism is required after the biomass is subject to mechanical disruption.

Also disclosed is a method for converting biomass into ethanol or other desired products. In one embodiment, the method includes (a) adding the biomass and a microorganism to a reactor, wherein the microorganism is capable of solubilizing the biomass and fermenting the solubilization products. In one aspect, the biomass contains lignocellulosic particles. In another embodiment, the method includes (b) mechanically disrupting the lignocellulosic particles of the biomass and (c) fermenting the biomass with the microorganism to produce desired fermentation products, such as ethanol, among others. In one aspect, steps (b) and (c) are performed simultaneously. In another aspect, step (b) is performed intermittently (for example, if mechanical disruption is carried out by conveying partially reacted solids from the fermentor to a mechanical disruption device and then either returned to the fermentor from which it was withdrawn or to a subsequent fermentor arranged in series).

In another embodiment, the disclosed method may include (a) adding a biomass and a microorganism to a reactor, (b) fermenting the biomass with the microorganism to form a first fermented product, (c) mechanically disrupting the first fermented product of step (b), and (d) fermenting the mechanically disrupted product of step (c), wherein steps (b)-(d) are repeated N times, and N is an integer equal to or greater than 1. In one aspect, N is in the range of from 1 to 10.

In another embodiment, the milling of fermented solids may be carried out at between about 8% and about 30% (w/w), for example, about 8%, 10%, 12%, 15%, 20%, or 30% (w/w) of solids.

In another embodiment, more than 50%, 60%, 65%, 70%, 75%, 80%, 90% or even 93% of carbohydrate in the biomass is solubilized via fermentation with intermittent or continuous mechanical disruption.

In another embodiment, one or more microorganisms may be used and the microorganisms are capable of fermenting the biomass to desired products. In another embodiment, the microorganisms are capable of solubilizing the biomass and fermenting the solubilization products. In another embodiment, the microorganism is insensitive to mechanical attack. In another embodiment, Gram positive microbes that have thicker cell walls than other microbes may be suitable for the disclosed process. The microbial system as disclosed herein may include pure culture or co-culture of microorganisms such as *Clostridium thermocellum*, *Clostridium claraflavum*, *Caldicellusiruptor bescii*, *Thermoanaerobacterium saccharolyticum*, *Thermoanaerobacterium thermosaccharolyticum*, *Thermobacterium ethanolicus*, similar saccharolytic thermophilic bacteria or combination thereof. By way of example, strains that may be used in the microbial system include but are not limited to *Clostridium thermocellum* DSM1313, *Clostridium thermocellum* ATCC 27405, *Clostridium claraflavum* 42A, *Clostridium claraflavum* DSM19732, among others. In one embodiment, engineered strains may be used in the disclosed processes to achieve higher yield and titer of ethanol or other desired product.

In another embodiment, the microbial fermentation and the mechanical disruption of the cellulosic material may occur simultaneously during fermentation. In another embodiment, the microbial fermentation and the mechanical disruption of the cellulosic material may occur sequentially, or intermittently, during fermentation.

In another embodiment, the system may use pressure developed in the reactor to power the means for mechanical disruption. The pressure may be from gas generated by fermentation in the reactor, or it may come from static pressure developed at the bottom of the fermentor. For instance, production of $CO_2$ by fermenting organisms may be contained and then released which may result in a transient increase in pressure. This increase in pressure may be used as a motive force to propel cellulosic slurries through an orifice (e.g. from one reactor to another, as in a cascade continuous configuration), or alternatively the sudden decrease of pressure may disrupt lignocellulosic particles as a result of formation of gas bubbles within the particles, which is similar to the process during making of popcorn.

Mechanical disruption of lignocellulosic particles may be achieved by a number of different ways. By way of example, the disruption may be accomplished by using solid particles (e.g. metal spheres) with density higher than water in the reactor (or fermentor). In another aspect, the disruption may be accomplished by exposure to shear by intense mixing, passage through an orifice or nozzle, or both. In another aspect, the disruption may be accomplished by pressure cycling, which may lead to formation of bubbles within cellulose particles due to supersaturated $CO_2$. In another aspect, the disruption may be accomplished by sending lignocellulosic particles through a mill (e.g. disc refiner, knife mill, roller mill or similar) outside of the fermentor and recycling particles back to the fermentor after the mechanical processing. In another aspect, the means for mechanically disruption and the powering means may include a nozzle or a hydrocyclone with dense beads.

In one embodiment, the means for mechanical disruption may comprise means selected from the group consisting of metal balls, metal beads, glass balls, glass beads, knife mill, disc mill, roller mill, hammer mill, a device allowing said biomass to flow through an orifice, a cyclone containing milling media with disruption carried out in the fermentor, and combination thereof. In another embodiment, the disclosed system may comprise a fermentor, a disrupting device external to the fermentor, and means for withdrawing particle-containing slurry from the fermentor, wherein the slurry is subject to mechanical disruption in the device and is returned either to the same fermentor from which the slurry is withdrawn or returned to a different fermentor.

In another embodiment, the means for mechanical disruption may include but are not limited to ball mill, disc refiner or both. In one aspect, metal or glass balls having a uniform diameter may be used. In another aspect, metal balls having different diameters may be used together to enhance the disruption. By way of example, metal balls having different diameters ranging from 2 mm to 50 mm, from 5 mm to 30 mm, or from 8 mm to 20 mm may be used.

DETAILED DESCRIPTION

Figure 1:
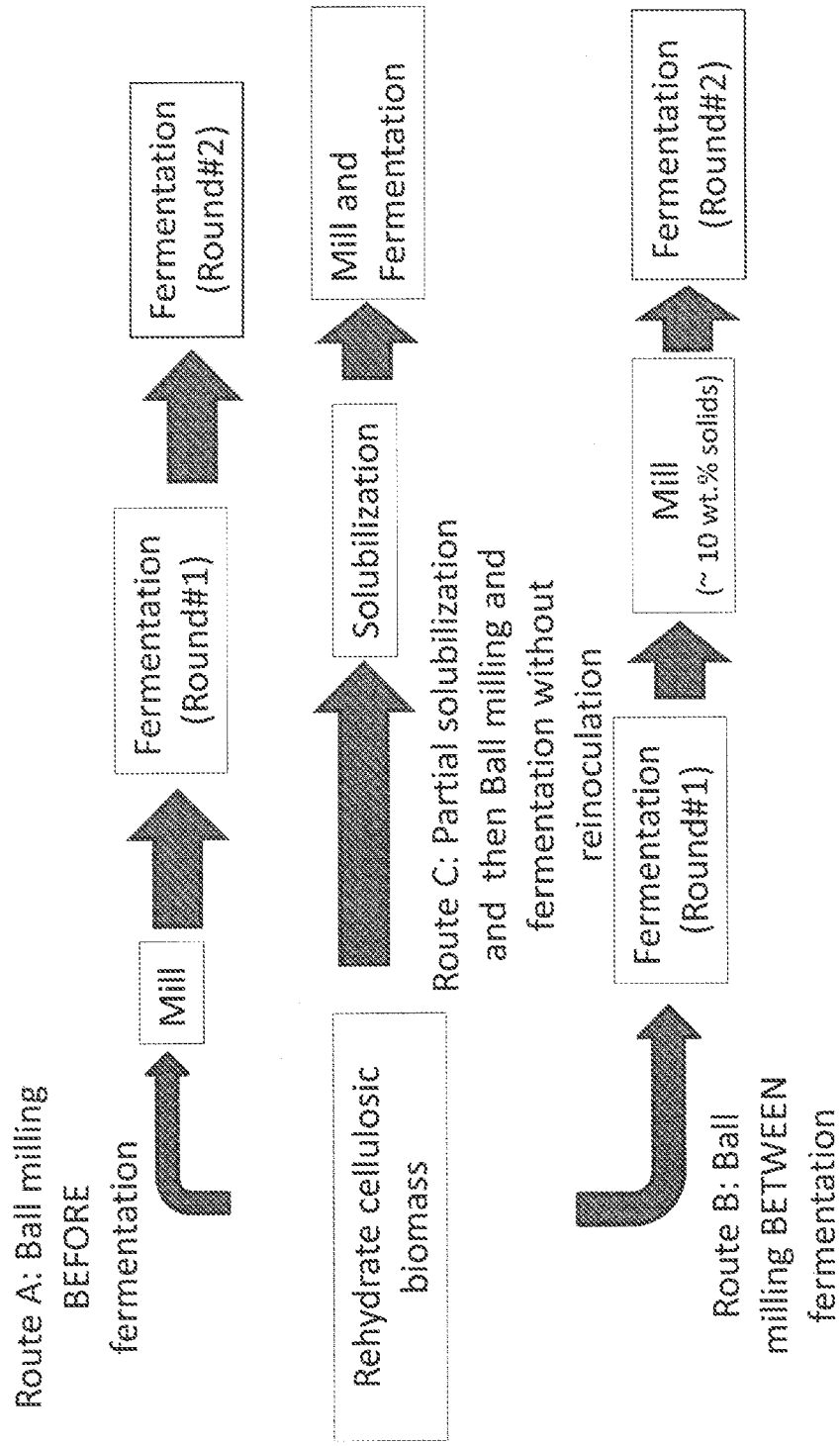
FIG. 1 is a flow chart showing, by way of examples, several embodiments of the co-treatment processes.

It is commonly believed in the field of cellulosic biofuel that pretreatment is required for effective biological conversion of cellulosic biomass to fuels or chemicals such as ethanol. Pretreatment adds to the cost and may affect performance during subsequent fermentation. Capital and operating costs for pretreatment are substantial, and pretreatment further increases processing costs by negatively impacting the performance of downstream processing operations. In particular, all known pretreatments either produce compounds which inhibit hydrolysis and fermentation or require recovery of chemical reagents (e.g. ammonia or ionic liquids), or both.

In addition to cost benefit, processing biomass without pretreatment may also foster recovery of co-products such as feed protein and high molecular weight lignin, and may make biomass processing substantially less hazardous. If cellulosic biomass can be processed with high yields and reasonably high rates without pretreatment, this would likely be a revolutionary advance resulting in processes that are much less expensive, simpler, and more reliable. Such an advance has clear potential to preempt other technical approaches and be of tremendous competitive advantage.

Potential disadvantages of biomass conversion with little or no pretreatment may include, for example, uncertainty about the impact of feedstock characteristics on amenability to processing, the possibility that solubilization will not be as effective at high concentrations, and that thermophiles cannot be engineered to achieve high ethanol yields and titers. It is disclosed here that high solubilization rates of cellulosic feedstocks may be achieved with little or no pretreatment by using cellulolytic microbes in conjunction with mechanical disruption of lignocellulose particles acting on partially-solubilized feedstocks.

The combination of microbial cellulose fermentation with mechanical disruption of partially solubilized lignocellulose particles has not been shown for the production of fuels or chemicals from cellulosic biomass. Physical disruption during solubilization mediated by cell-free enzyme preparations has been demonstrated. See, e.g. Ryu and Lee, Biotechnol Bioeng. 1983, 25(1):53-65; Jones and Lee, Biotechnol Bioeng. 1988, 31(1):35-40; Tjerneld et al., Bioseparation. 1990, 1(3-4):255-63. However, these studies did not use fermentation as disclosed herein. More importantly, it is not known whether fermenting microbes would survive mechanical disruption (e.g., milling) at intensities sufficient to substantially impact solubilization. The present disclosure shows that microbial conversion with no added enzymes and in conjunction with mechanical disruption is possible without negatively impacting fermentation.

In another aspect, all prior studies used an attrition reactor with added enzymes. Certain limitations have been observed in studies of enzymatic hydrolysis in an attrition reactor. These limitations include, by way of example, the cost of added enzymes, decreased effectiveness at high solids, and inhibition of enzymes by hydrolysis products, among others. These limitations associated with cell-free enzymatic hydrolysis in an attrition reactor may be less important in a microbial system because of the different mechanisms involved in the two systems.

In another aspect, combined microbial conversion and mechanical disruption is likely to be both less expensive and more effective as compared to milling prior to conversion because of (a) the weakening of the particles during conversion, which is expected to make them considerably easier to disrupt as compared to disruption prior to conversion, (b) the radically reduced viscosity of lignocellulose slurries upon conversion, and (c) the generation of new surfaces during the reaction process.

The term "biomass" refers here to non-fossilized renewable materials that are derived from or produced by living organisms. In its broadest term, biomass may include animal biomass, plant biomass, and human waste and recycled materials, among others. Examples of animal biomass may include animal by-product and animal waste, etc. In one embodiment of this disclosure, biomass refers to plant biomass which includes any plant-derived matter (woody or non-woody) that is available on a sustainable basis. Plant biomass may include, but is not limited to, agricultural crop wastes and residues such as corn stover, wheat straw, rice straw, sugar cane bagasse and the like, herbaceous crops, such as switchgrass, *miscanthus*, energy cane, alfalfa, winter rye, and the like. Plant biomass may further include, but is not limited to, woody energy crops (e.g. poplar, willow, *eucalyptus*), wood wastes and residues such as trees, forest thinnings, bark wastes, sawdust, paper and pulp industry residues or waste streams, wood fiber, and the like. In urban areas, plant biomass may include yard waste, such as grass clippings, leaves, tree clippings, brush, etc., vegetable processing waste, and waste cardboard and paper.

In one embodiment, grassy biomass may be used in the present disclosure. In another embodiment, winter cover crops such as winter rye may be used as a bioenergy feedstock using existing equipment and knowhow. Winter cover crops have little and arguably no competition with food crops for land or revenue, and they also positively impact soil and water quality as well as farm income, and offer important co-product opportunities. A recent study estimated that 200 million dry tons of winter rye per year could be produced in the U.S. on land used to grow corn and soybeans, which has a liquid fuel production potential equal to that of the current U.S. and Brazilian industries combined.

By using the system and methods disclosed herein, other cellulosic feedstocks may also be processed into biofuels without pretreatment. Examples of microorganisms may include but are not limited to *C. thermocellum, C. clarafal-vum, C. bescii* or *C. thermocellum/Thermoanaerobacterium saccharolyticum* co-culture as fermentation systems. Various strategies for mechanical augmentation may be employed to further enhance the conversion. These strategies may include, by way of example, in situ ball-milling, passage through a nozzle or a high-shear in-line mixer, milling with a knife mill, roller mill or similar either in the fermentor or in an auxiliary vessel, and several configurations involving use of pressure developed during fermentation as a motive force. The use of microbial cellulose fermentation in conjunction with mechanical disruption may prove to be a cost-effective and efficient way for enhancing biomass conversion.

For purpose of this disclosure, the term "pretreatment" refers to the process of exposing cellulosic biomass to conditions—including but not limited to high temperature and/or chemicals—in order to increase solubilization yield upon subsequent biological processing. For purpose of this disclosure, the term "pretreatment" does not include autoclaving (or heat sterilization).

It will be readily apparent to those skilled in the art that the systems and methods described herein may be modified and substitutions may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Example 1

Mechanical Disruption Contributed to Higher Solubilization Rates

FIG. 1 is a flow chart showing the different routes of the combined mechanical and microbial treatment process. In Route 1, the biomass is subject to ball milling before fermentation. In Route 2, the biomass is subject to ball milling between the two Rounds of fermentations. In Route 3, milling is performed on partially solubilized biomass, without the need to reinoculate the microorganism after milling.

Figure 2:
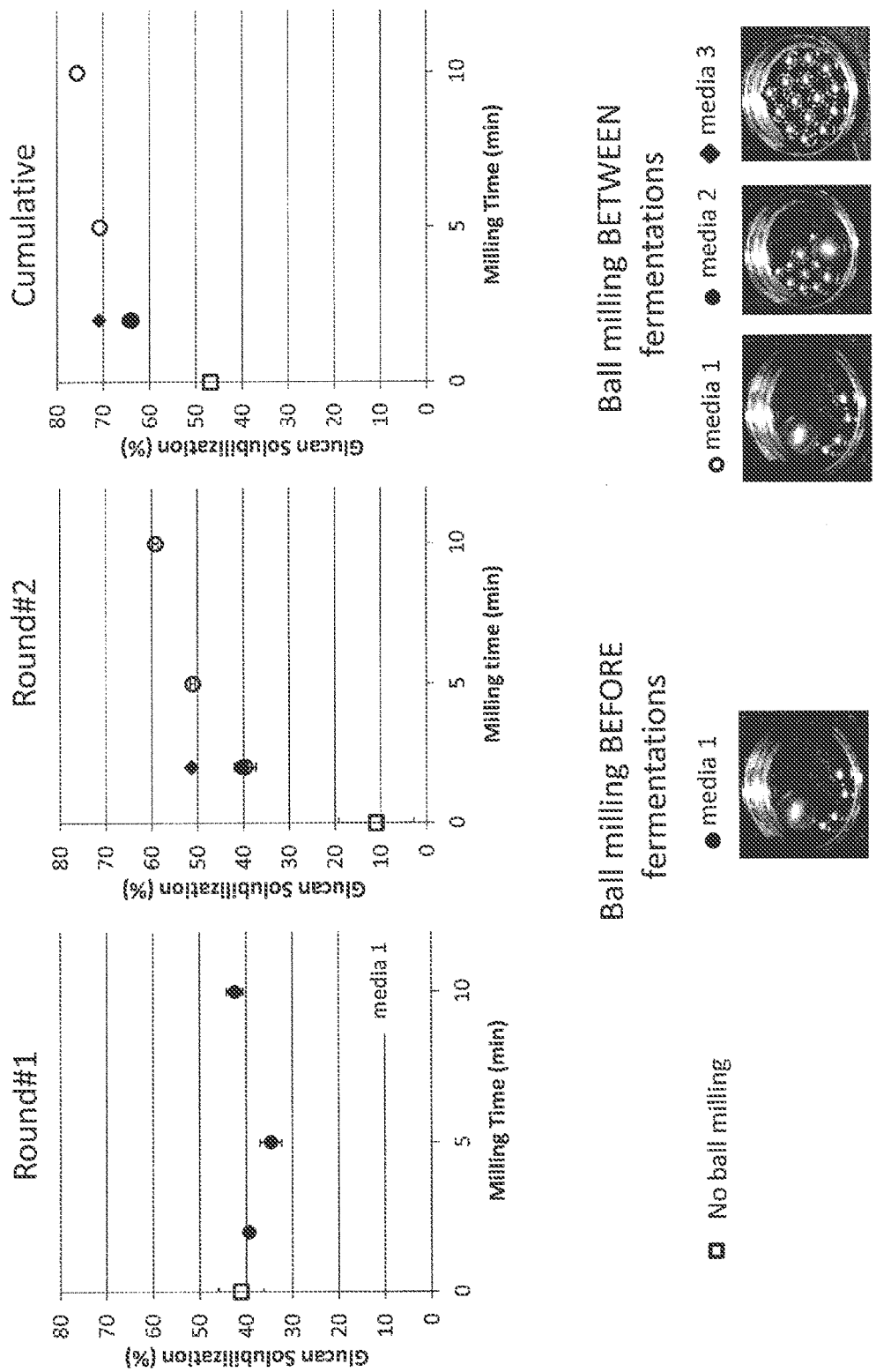
FIG. 2 shows glucan solubilization results after Round 1 and Round 2 for each of the two Routes 1 and 2, respectively, as shown in FIG. 1. The Cumulative glucan solubilization is also shown.

FIG. 2 shows glucan solubilization results after Round 1 and Round 2 for Routes 1 and 2, respectively. The Cumulative glucan solubilization is also shown in FIG. 2. The diameters of the balls in media 1 and 2 were 8 mm, 11 mm, and 20 mm. The diameter of the balls in media 3 was 11 mm.

Example 2

Comparing Solubilization Results of SSF and Various Microorganisms

Figure 3:
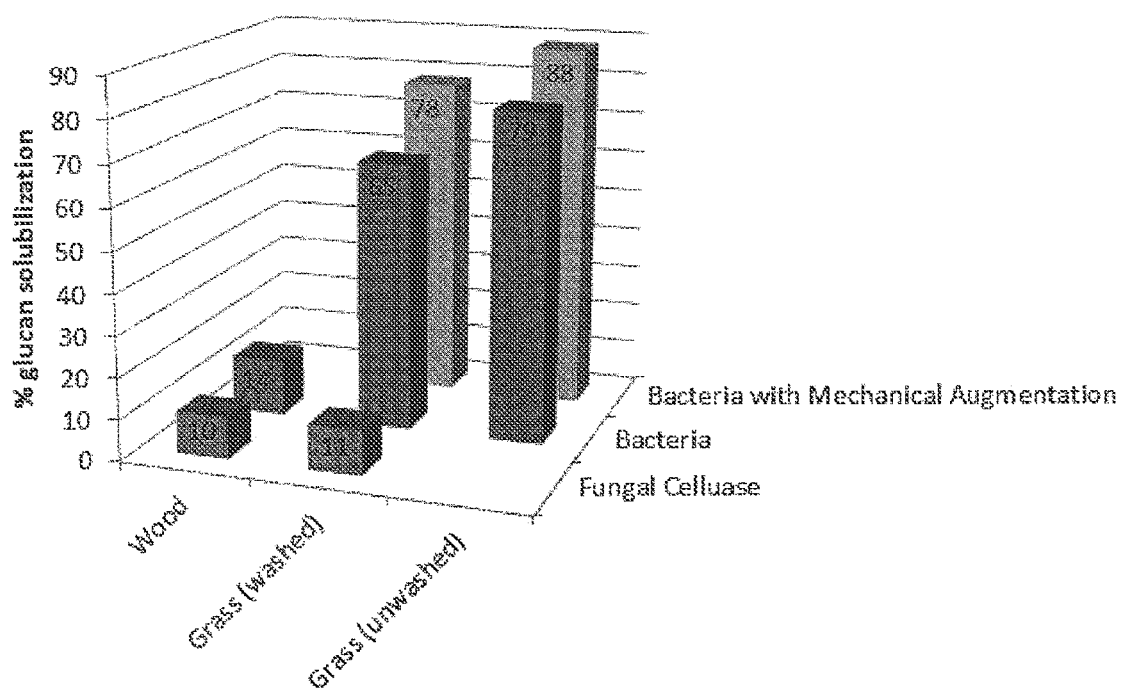
FIG. 3 shows the high conversions achieved by bacterial/microbial conversion and enhanced by mechanical force on grass (washed or unwashed) compared to the much lower conversions obtained from SSF featuring added fungal cellulase on wood or grass.

Experiments were conducted to compare the solubilization results using simultaneous saccharification and fermentation with fungal cellulase and yeast (SSF) and various microorganisms. FIG. 3 highlights the differences between enzymatic and microbial conversion on untreated woody versus grassy lignocellulose. While performances of fungal cellulases were similar between untreated wood and grass (10% vs 11%), microbial conversions of untreated grass were over 4 times greater on grass than conversion of wood using fungal cellulase. Conversion was further increased to 78% by introducing a means of mechanical disruption/ augmentation. The results labeled "washed" were performed on switchgrass in which soluble glucans were removed (60 C overnight wash). Glucan solubilization for bacteria with mechanical augmentation was 88% for unwashed switchgrass (FIG. 3).

As shown in FIG. 3, microbial cellulose conversion shows superior hydrolysis performance on untreated or minimally-pretreated substrates when compared to conventional systems using fungal cellulases. Microbial conversion combined with mechanical disruption during conversion may be more effective than microbial conversion without mechanical disruption. As shown in FIG. 3, microbial conversion may achieve about 65% conversion or greater in the absence of mechanical disruption. Higher extents of solubilization may be achieved when mechanical disruption is employed.

While solubilization yields for un-pretreated switchgrass typically need to be increased by greater than 5-fold in order to achieve the high extents of solubilization generally required for attractive economics, an increase of only 30% or so in a microbial cellulose system may be sufficiently cost-effective. Thus, while a relatively small intensity of mechanical disruption may be required for microbial conversion, much more severe disruption may be required for conversion of unpretreated substrates using fungal cellulases.

Example 3

Comparing Solubilization Results of Various Microorganisms

Figure 4:
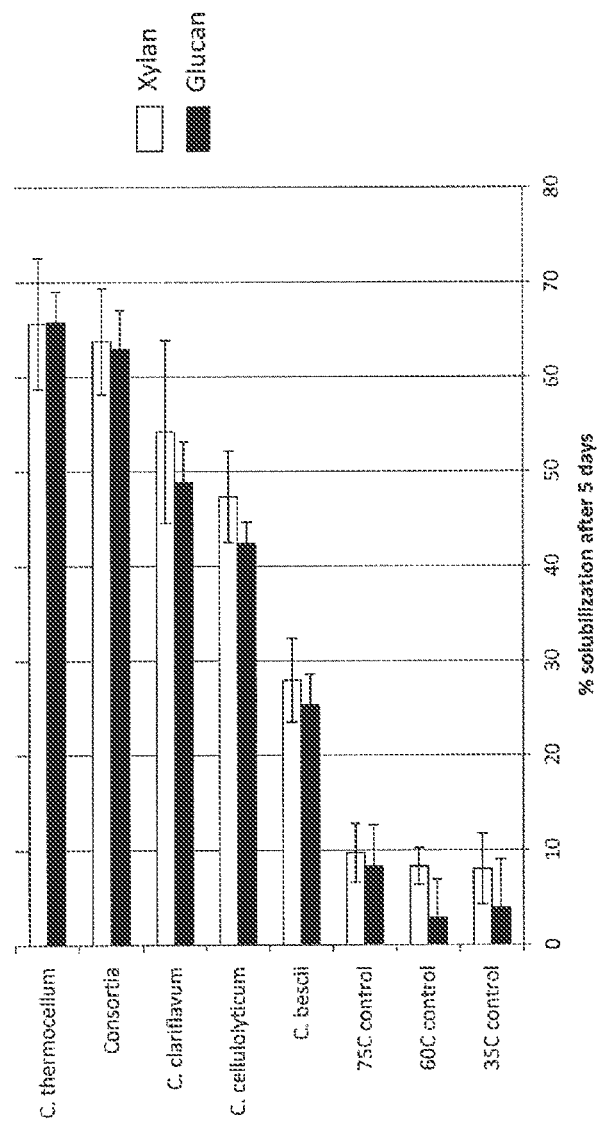
FIG. 4 shows results comparing solubilization of the switchgrass after 5-day treatment with different microorganisms.

Solubilization results using various feedstocks (switchgrass and poplar) and conversion systems (*C. thermocellum* & SSF with fungal cellulase, *C. bescii*, *C. clariflavum*, *C. cellulolyticum*, mixed enrichment) were examined and compared. Solubilization of autoclaved but not otherwise pretreated washed switchgrass harvested in mid-June was examined using a number of biocatalysts. FIG. 4 shows the comparative results comparing solubilization of the switchgrass after 5-day treatment with different microorganisms. Parameters for these tests were: 5 g/L glucan, 13 g/L solid, <4 mm particle size, 2% inoculum after 5 days in serum vials. The consortia were enriched at 60 C from horse manure compost with Avicel (a microcrystalline cellulose) as the substrate. Results are expressed as mean+/− standard deviation for three independent tests each carried out in triplicate. As shown in FIG. 4, *C. thermocellum* and the consortia both showed about 65% solubilization, while other microorganisms tested showed lower solubilization percentages.

Figure 5:
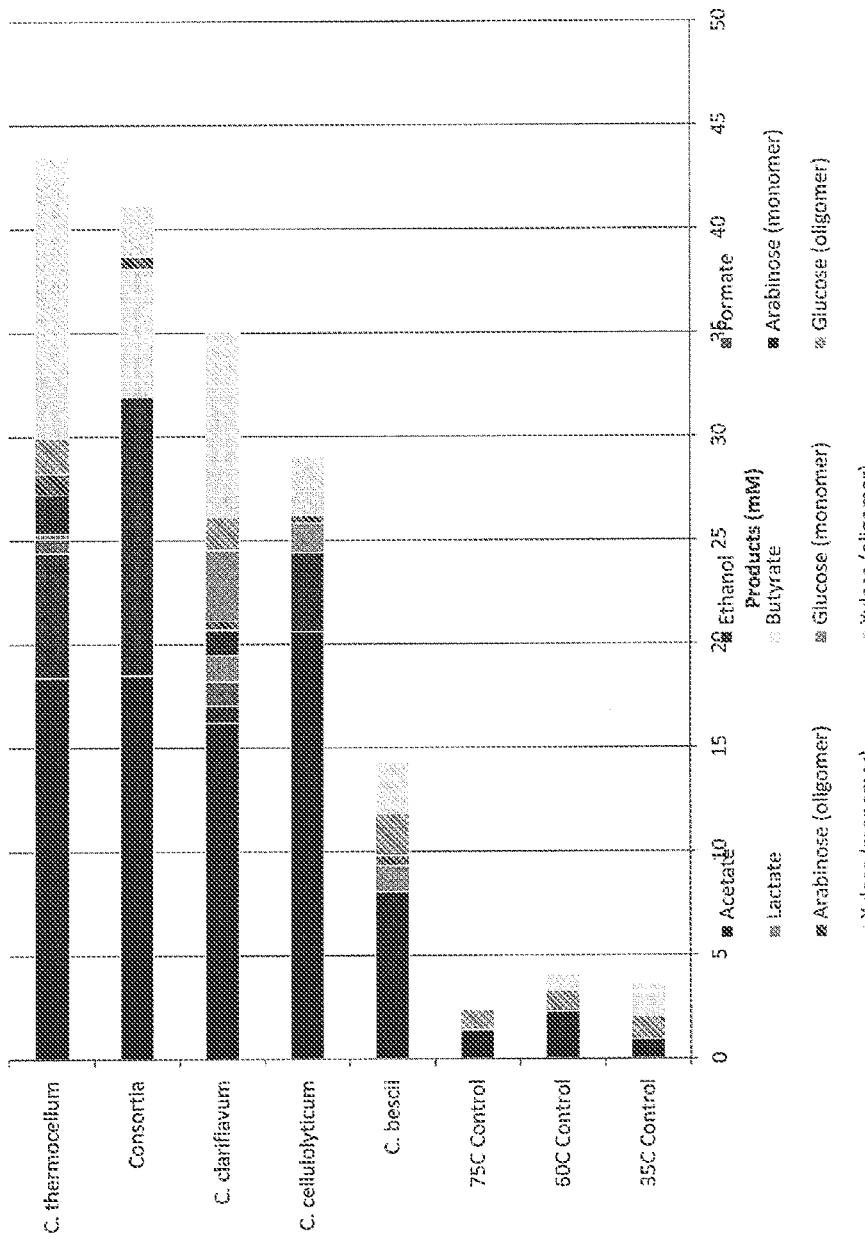
FIG. 5 shows the various products from the solubilization and conversion experiments described in FIG. 4.

FIG. 5 shows the solubilization products for the experiments in FIG. 4. Fermentation and hydrolysis products from washed green switchgrass (4 mm particle size) by various microorganisms (2% inoculum) after 5 days. Consortia were enriched on Avicel from horse manure compost. Results are expressed as mean (n=3). As shown in FIG. 5, acetate was present at highest concentrations for all cultures and controls. Soluble sugars were present at significant levels for all cultures except the consortium (no pH control).

Example 4

Figure 6:
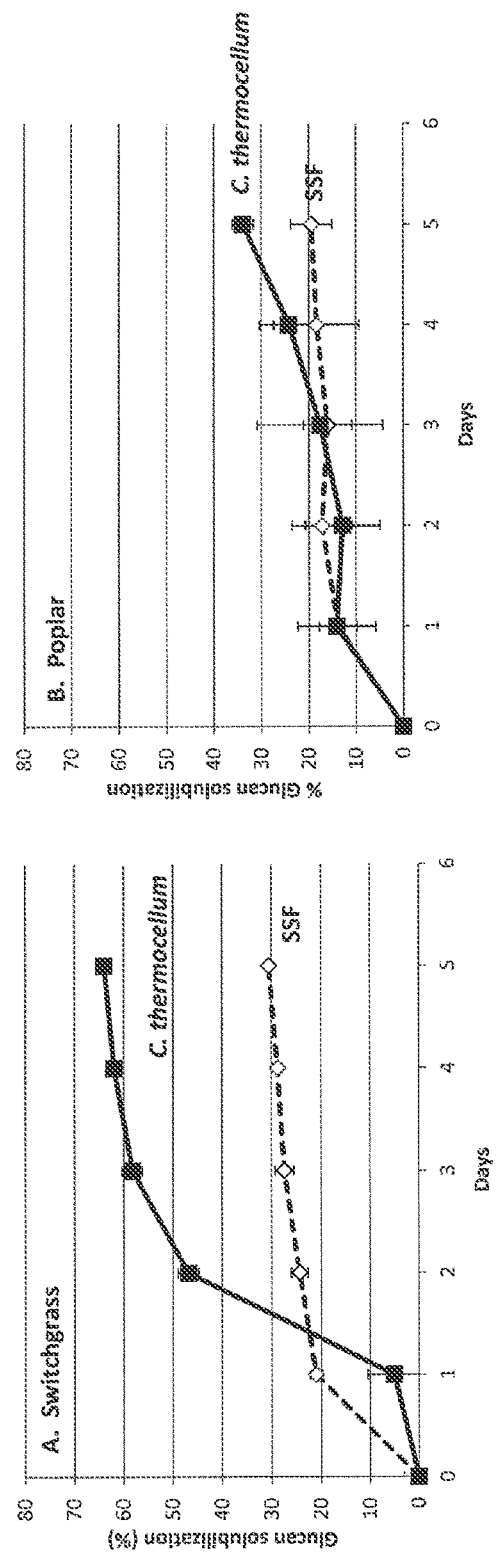
FIG. 6 shows comparative glucan solubilization results of autoclaved but not otherwise pretreated mid-June harvested switchgrass and poplar by *C. thermocellum* and by SSF using fungal cellulase and yeast.

Comparing Solubilization Results of Different Biomass Using Different Microorganisms and SSF Glucan solubilization of autoclaved but not otherwise pretreated mid-June harvested switchgrass and poplar by different microorganisms or cellulase was examined. Results of *C. thermocellum* and SSF using fungal cellulase and yeast are shown in FIG. 6. The tests were conducted in serum vials for 5-day incubation. Fungal cellulase loadings were 4.5 mg Ctec2 per gram solid and 0.5 mg Htec2 per gram solid. Solubilization of uninoculated switchgrass (5 g/L glucan, 13 g/L solid, <4 mm particle size) and poplar (5 g/L glucan, 11 g/L solid, <0.5 mm particle size) was less than 10%. Results are expressed as mean+/− standard deviation for three independent experiments each carried out in triplicate. As shown in FIG. 6, *C. thermocellum* conversion exceeded SSF by about 2-fold at low enzyme loading, and mid-June switchgrass was much more reactive than wood for both systems.

Example 5 Effects of the Amount of Solid Loading on Solubilization

The impact of reduced solids loading on solubilization was studied. Glucan solubilization from washed mid June-harvested switchgrass with an initial solids concentration of 13 g/L or 2.5 g/L after 5 days was compared. Fungal cellulase loading was 4.5 mg Ctec2/g solid and 0.5 mg Htec2/g solid. Results are expressed as mean+/−standard deviation for three independent experiments each carried out in triplicate.

Figure 7:
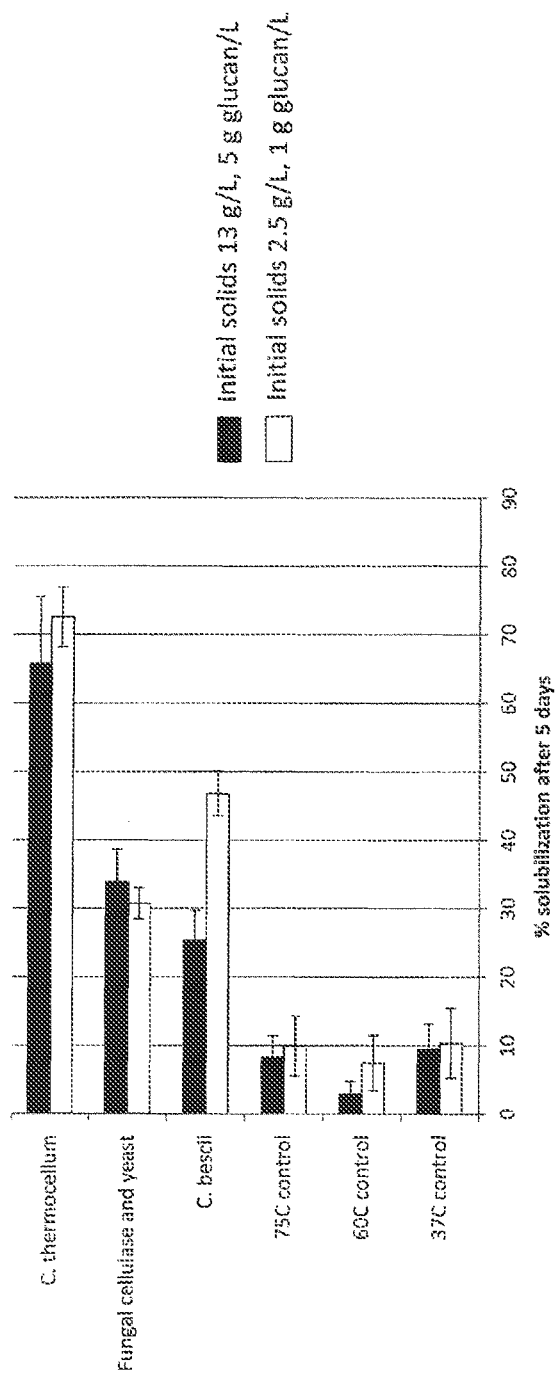
FIG. 7 shows the impact of reduced solids loading on solubilization.

As shown in FIG. 7, initial solids loading had a significant impact on glucan solubilization for *C. bescii*, but not for *C. thermocellum* or SSF.

Example 6

Effects of Biomass Harvest Date and Particle Size on Solubilization

Glucan solubilization for washed, autoclaved but not otherwise pretreated feedstocks as a function of harvest switchgrass harvest date, choice of biocatalyst, and particle size was studied. *C. thermocellum* (filled squares) or fungal cellulase and yeast (open diamonds), with 5 day incubation in serum vials was used in the study. Fungal cellulase loading was 4.5 mg Ctec2/g solid and 0.5 mg Htec2/g solid. Solubilization of uninoculated young switchgrass (5 g/L glucan, 13 g/L solid), senescent switchgrass (5 g/L glucan, 12 g/L solid) and poplar (5 g/L glucan, 11 g/L solid) was less than 10%. Results are expressed as mean+/−standard deviation for three independent experiments each carried out in triplicate.

Figure 8:
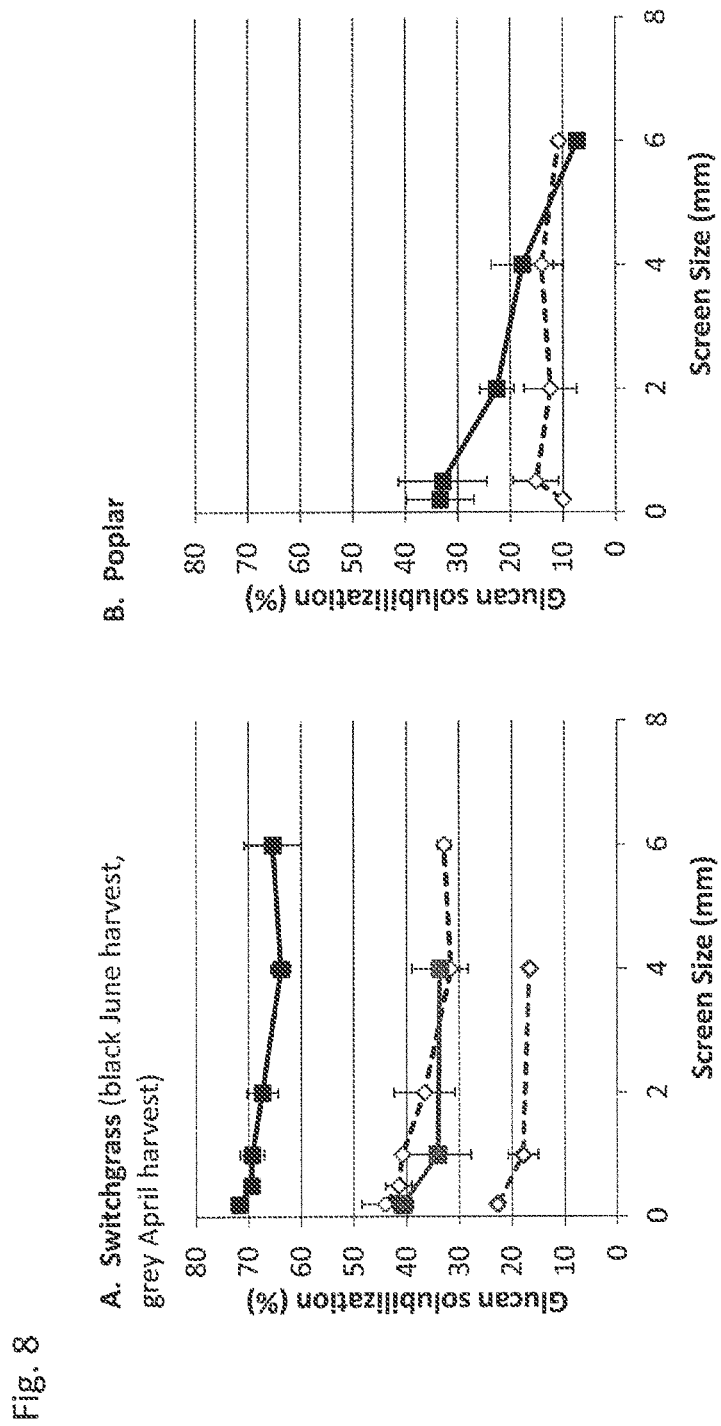
FIG. 8 shows the effects of harvest date, choice of biocatalyst, and particle size on glucan solubilization for washed, autoclaved but not otherwise pretreated feedstocks.

As shown in FIG. 8, particle size did not show a significant impact for grass, poplar SSF. However, particle size appeared to have some significant impact for *C. thermocellum* on poplar.

Solubilization of senescent switchgrass was about half that of mid-June harvested switchgrass for both *C. thermocellum* and SSF, suggesting that harvest date also has a significant impact on solubilization. Here again, *C. thermocellum* was about 2 times as effective as SSF on swtichgrass at all particle sizes and at both maturities.

Example 7

Effects of Enzyme Loading and Source of Enzymes on Solubilization

Comparative glucan solubilization from autoclaved but not otherwise pretreated mid June-harvested switchgrass by various loadings of *C. thermocellum* enzymes or fungal cellulase after 5 days in serum vials. 5 g/L glucan, 13 g/L solid, 4 mm particle size.

*C. thermocellum* enzymes were purified by either affinity purification (○) or by concentrating and dialyzing cell-free broth (●). Fungal cellulase was incubated at 37 C in the presence (X) or absence of yeast (□), at lower substrate concentration (Δ, 2.5 g/L solids), or increased hydrolysis temperature (◇, 50 C). Results are expressed as mean+/−standard deviation (n=3 for fungal cellulase, n=2 for affinity purified cellulase, n=1 for dialyzed concentrated broth).

Figure 9:
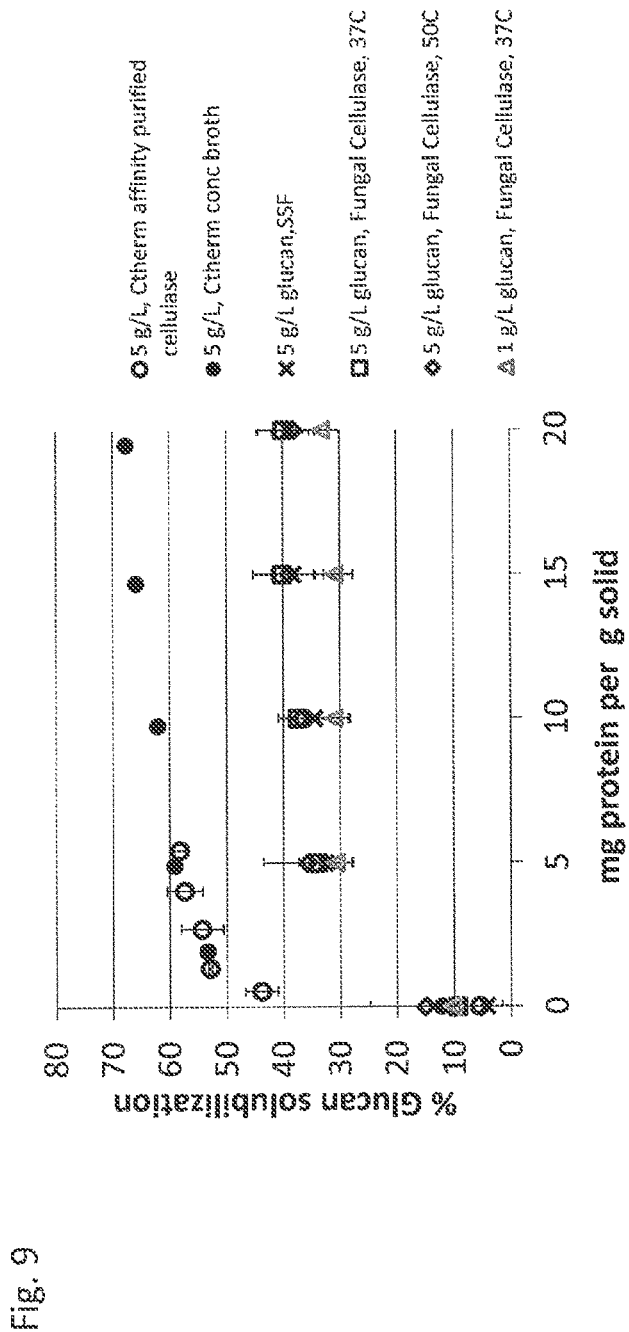
FIG. 9 shows comparative glucan solubilization from autoclaved but not otherwise pretreated mid June-harvested switchgrass by various loadings of *C. thermocellum* enzymes or fungal cellulase after 5 days in serum vials.

As shown in FIG. 9, 5 day SSF solubilization was not significantly improved by the presence or absence of yeast, higher enzyme loadings, higher incubation temperature, or lower feedstock loading. *C thermocellum* cellulase was much more effective than fungal cellulase at all loadings.

Example 8

Comparative Evaluation of Biocatalysts and Enhancement Via Cotreatment

The ability of various biocatalysts to solubilize autoclaved but otherwise unpretreated cellulosic biomass was examined under controlled but not industrial conditions. Carbohydrate solubilization of mid-season harvested switchgrass after 5 days ranged from 24% for *Caldicellulosiruptor bescii* to 65% for *Clostridium thermocellum*, with intermediate values for a thermophilic horse manure enrichment, *Clostridium clariflavum*, *Clostridium cellulolyticum*, and simultaneous saccharification and fermentation (SSF) featuring a fungal cellulase cocktail and yeast. Solubilization yields were about twice as high for *C. thermocellum* compared to fungal cellulase regardless of enzyme loading, the presence or absence of microbes, fungal cellulase incubation temperature, substrate particle size, and initial substrate loading. Solubilization of mid-season harvested switchgrass was about twice that of senescent switchgrass. Lower yields and greater dependence on particle size were observed for *Populus* as compared to switchgrass. Trends observed from data drawn from six conversion systems and three substrates, including both time course and end-point data, were: 1) equal fractional solubilization of glucan and xylan, 2) no biological solubilization of the non-carbohydrate fraction, and 3) higher solubilization for three of the four bacterial cultures tested as compared to the fungal cellulase system.

Brief (5 minute) ball milling of solids remaining after fermentation of senescent switchgrass by *C. thermocellum* nearly doubled carbohydrate solubilization upon reinoculation as compared to a control without milling. Greater particle size reduction and solubilization were observed for milling of partially-fermented solids than for milling unfermented solids.

Biologically-mediated processing of cellulosic biomass is a promising route to sustainable production of fuels and chemicals, but requires improved approaches to producing soluble intermediates from this recalcitrant feedstock. In the most comprehensive comparative study of microbial cellulose utilization to date, a greater than expected difference in solubilization efficacy was observed depending on the choice of microorganism and feedstock, and in particular that fermentation by several cultures of anaerobic bacteria is substantially more effective than industry-standard fungal cellulase over a broad range of conditions. These results provide mechanistic insights and also show that pretreatment featuring elevated temperatures and/or chemical addition may be avoided by combining appropriate cellulolytic microbes with physical disruption either simultaneously with fermentation or after partial fermentation.

The extent of microbially-mediated solubilization of lignocellulosic substrates was documented under controlled, but not industrial conditions, in the most comprehensive such comparative study to date. The glucan and xylan solubilization yields obtained by three bacterial cultures (*C. thermocellum*, *C. clariflavum*, and *C. cellulolyticum*) were substantially higher (FIG. 10) than the yields obtained by fungal cellulase and yeast. At an initial substrate concentration of 5 g glucan/L, the extreme thermophile *C. bescii* exhibited the lowest solubilization of the systems tested. However, at an initial glucan concentration of 1 g/L, *C. bescii* exhibited higher solubilization than the SSF, suggesting that this organism has strong intrinsic biomass solubilization capability but that growth and/or enzymes are more susceptible to inhibition. A strong correlation between the rate of microbial growth on model cellulosic substrates with increasing temperature has previously been observed (Ref #35), although conditions were not controlled. Although the highest solubilization yields observed herein were at 60 degrees (*C. thermocellum* and the horse manure enrichment), the range of yields observed for thermophilic systems overlapped that for mesophilic systems.

The observation here of roughly 2-fold higher lignocellulose solubilization yields for *C. thermocellum* as compared to SSF on microporous lignocellulosic substrates is remarkable—and as yet not understood—in light of the much larger size of the *C. thermocellum* cellulosome complex as compared to the components of the non-complexed *T. reesei* cellulase system. Little response to increased enzyme loading above 5 mg/g mid-season switchgrass was observed for either fungal or *C. thermocellum* cellulases. A large response over this range has been observed for fungal cellulases acting on pretreated substrates, as might be expected due to increased substrate accessibility following pretreatment. See Wyman et al., 2011; Elander et al., 2009, and Wyman et al., 2009. The presently disclosed results differ from those of Resch et al., who reported similar solubilization of minimally pretreated senescent switchgrass by equal loadings of either fungal or *C. thermocellum* cellulases Resch et al., 2013.

Figure 10:
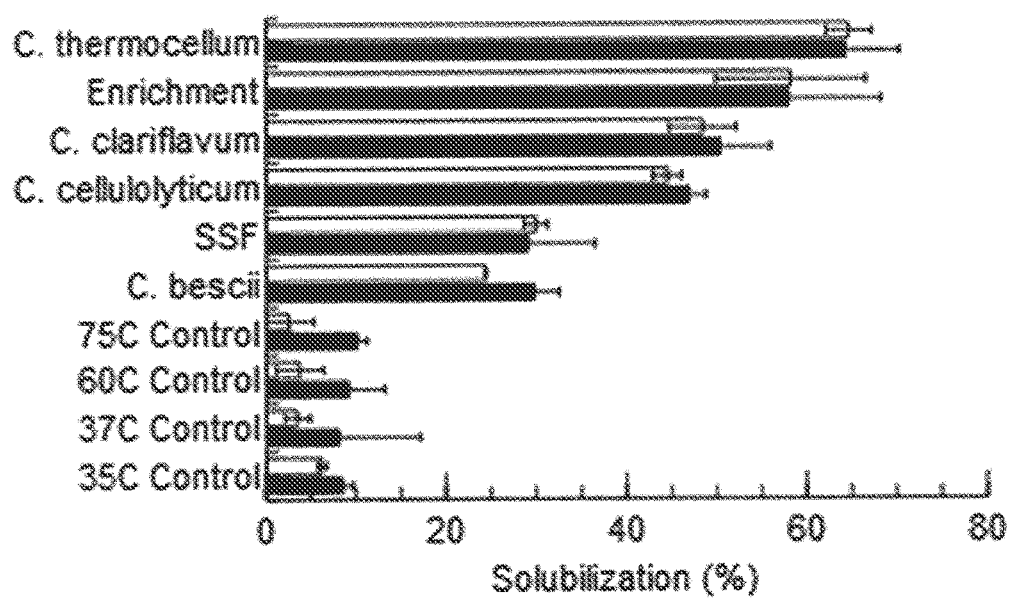
FIG. 10 shows Solubilization of xylan (white) and glucan (black) from washed mid-season switchgrass by various bacteria or SSF with yeast and fungal cellulase after 5 days. Enrichment was selected at 60 C on Avicel from horse manure compost. Uninoculated controls for each incubation temperature were analyzed to account for non-biological solubilization. Results are expressed as mean±SD (n≥2).
Figure 11:
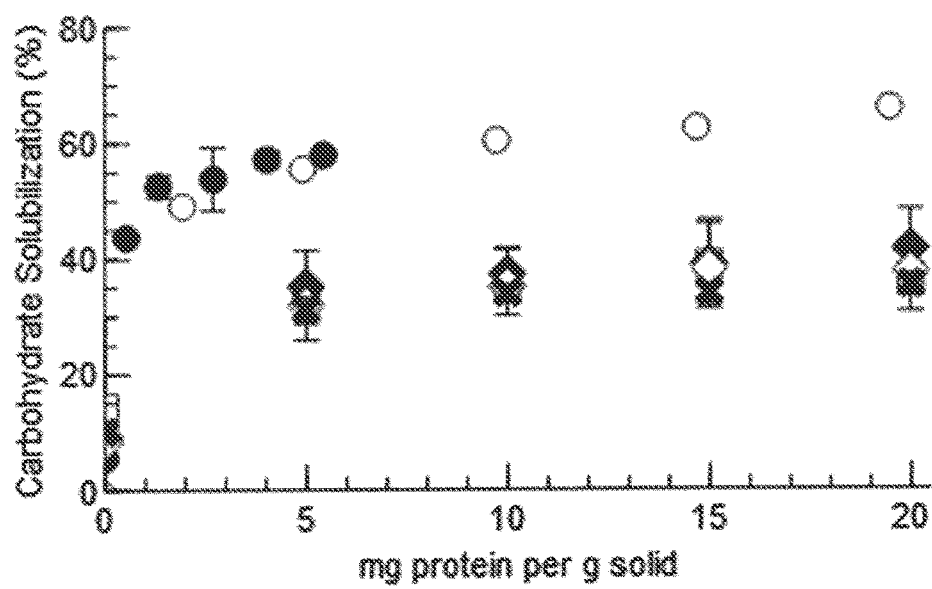
FIG. 11 shows Carbohydrate solubilization from washed mid-season by various loadings of *C. thermocellum* enzymes (blue) or fungal cellulase (red) after 5 days. *C. thermocellum* enzymes were purified by either affinity purification (○) or by concentrating and dialyzing cell-free broth (●). Fungal cellulase was incubated at 37 C in the presence (♦) or absence of yeast (◇), at lower substrate concentration (X, 1 g/L glucan, 2.5 g/L solids), or increased hydrolysis temperature (□, 50 C). Results are expressed as mean±SD (n≥2 except for dialyzed concentrated broth).
Figure 12:
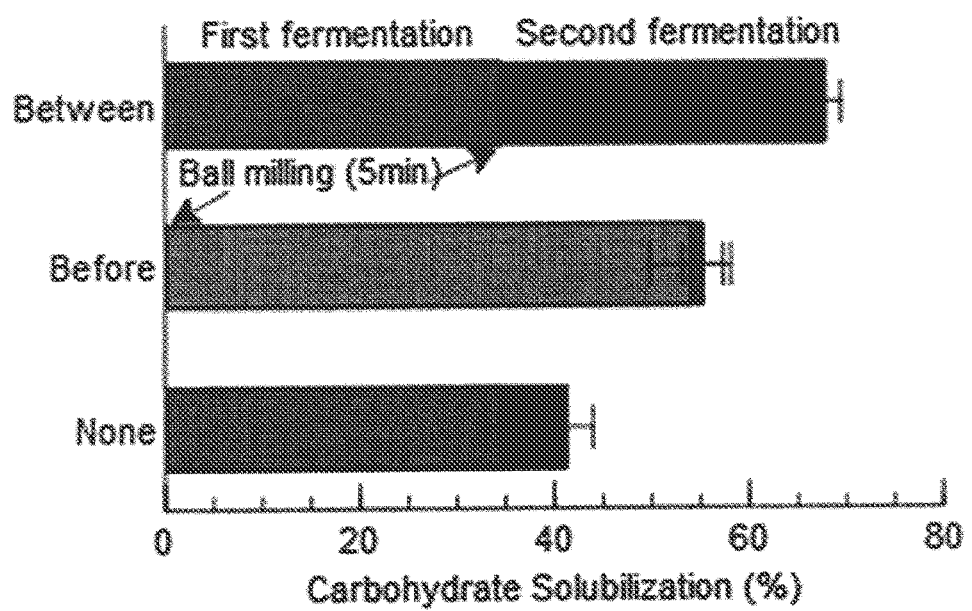
FIG. 12 shows carbohydrate solubilization of washed senescent switchgrass (Alamo) during successive 5 day fermentations as described in the text. Green: milling between first and second fermentation. Red: milling before the first fermentation. Blue: no milling. Results are expressed as mean±SD (n≥2).
Figure 13:
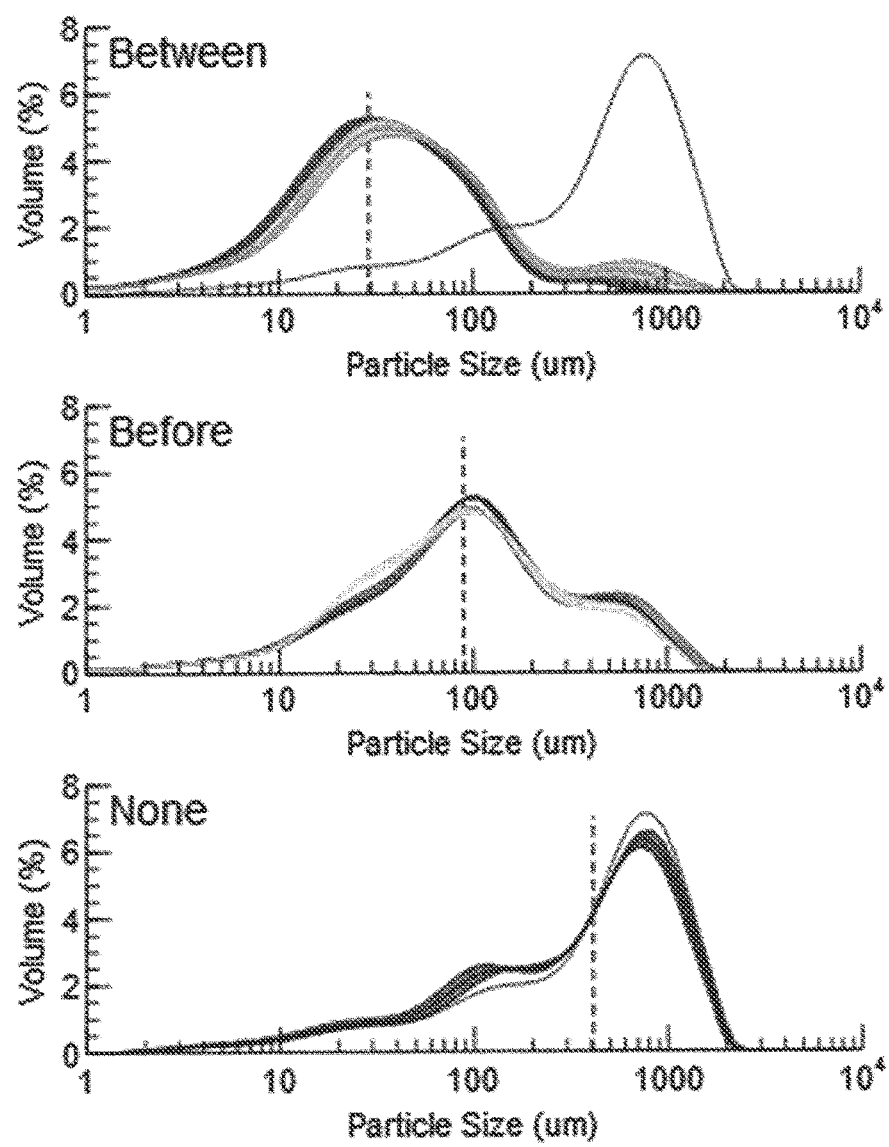
FIG. 13 shows particle size distributions of residual solids from *C. thermocellum* fermentation of washed senescent switchgrass without (blue) or with brief milling before (red) or after (green) partial fermentation (see FIG. 4). Particle size distribution (mean±SD, n≥2 except for no milling condition after 1 fermentation stage) is show for each milling condition either after one (moderate hue) or two (darkest hue) fermentation stages. Measurement of initial partial size distribution was only possible for the milling before condition (lightest color hue). Volume-mean particle size after two fermentations is indicated by the dashed line for each milling condition.
Figure 14:
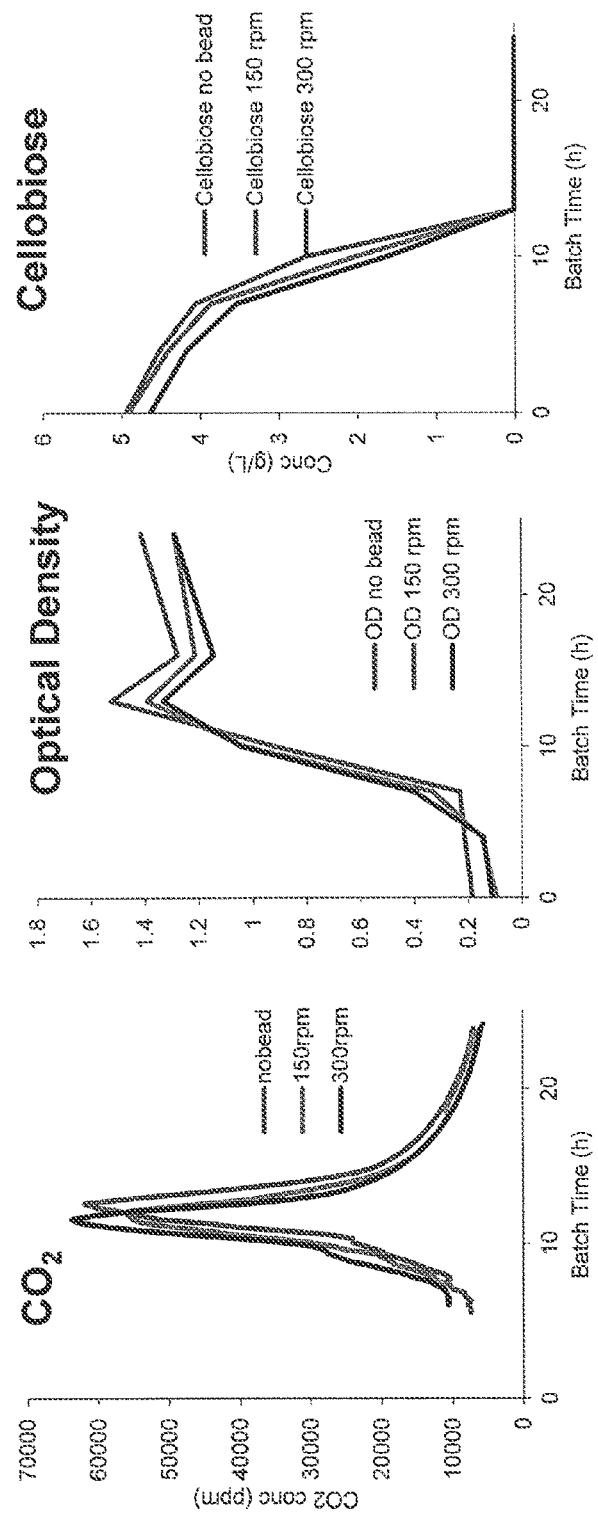
FIG. 14 shows that growth and substrate utilization is not adversely affected by the disclosed co-treatment methods.
Figure 15:
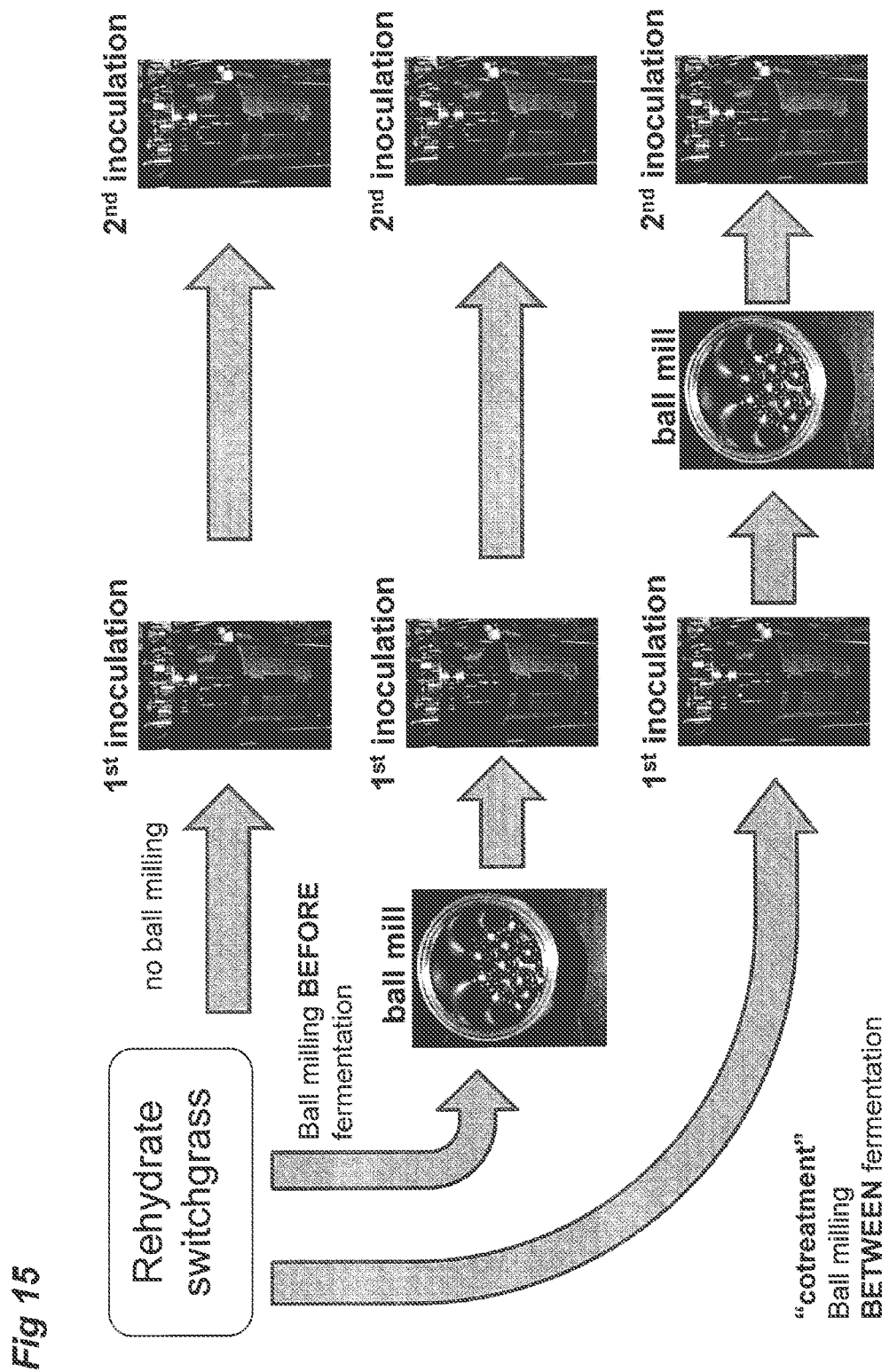
FIG. 15 shows a schematic representation of the disclosed co-treatment methods-Mechanically disrupt lignocellulose during reaction.

Enhanced rates of cellulose solubilization have been observed in the presence of metabolically active microorganisms as compared to cell-free enzyme systems (Refs #29 and 30). No increased extents of solubilization in experiments involving actively fermenting cells as compared to cell-free cellulase preparations were observed. Adding high levels of *C. thermocellum* cellulase (FIG. 11) does not result in higher 5-day solubilization as compared to microbial cultures (FIG. 10). The results reported here do not preclude such enzyme-microbe synergy with respect to the rate of biomass solubilization.

Since even the most effective systems examined here achieve less than 40% solubilization of senescent switchgrass under favorable conditions, it is logical to look to non-biological strategies to increase solubilization. Disruption of the lignocellulose matrix prior to biological processing (pretreatment) has been investigated extensively. Considerably less attention has been given to non-biological disruption after biological attack has begun, or "cotreatment". As noted by Weimer et al. (Ref #38), alternating mechanical and biological disruption are important factors underlying the high solubilization of grass realized by ruminants, and this approach has promise in the context of industrial processes.

Brief ball milling of residual solids from fermentation of senescent switchgrass by *C. thermocellum* followed by a second fermentation nearly doubled overall solubilization yields as compared to that achieved after a single fermentation without ball milling. It is notable that the fractional solubilization of carbohydrate present at the start of the respective fermentation was higher for the second fermentation (51±2%) than for the first fermentation (35±2%). The main observed effect of milling was decreased particle size. Little impact of brief milling on crystallinity was observed, consistent with prior reports (Refs #20, 39 and 40). These results highlight the importance of accessibility in determining hydrolysis yields. Milling after partial biological solubilization was more effective at enhancing solubilization than milling prior to fermentation, as have others (Refs #14 and 15), and also found that milling after partial solubilization was more effective at reducing particle size. The substantial impact of brief milling observed here supports the possibility of mechanical disruption in a vessel much smaller than the fermentor. By contrast, prior investigations of cotreatment, under various names, have generally employed continuous milling (Refs #14-16) requiring that milling occur in the hydrolysis reactor or a comparably-sized vessel. Whereas we studied the impact of milling during fermentation, prior reports using milling to enhance solubilization of lignocellulose have focused on enzymatic hydrolysis in the absence of cells.

Because partially-reacted substrate particles have decreased mass, viscosity, and mechanical integrity compared to unreacted solids, mechanical disruption during fermentation was more effective and require less energy than disruption prior to biological attack.

Biocatalysts.

*C. thermocellum* strain DSM 1313, DC3 enrichment (Ref #42), and *C. clariflavum* DSM 19732 were cultured in LC media as described previously (Ref #43) with 5 g/L MOPS and 1 g/L L-cysteine hydrochloride monohydrate at 60° C. For experiments with *Populus*, *C. thermocellum* was cultured in MTC as previously described (Ref #43) since growth was more reliable than in LC media. *C. cellulolyticum* H10 was cultured a modified CM3 media (Ref #44) at 35° C. and *C. bescii* DSM 6725 was cultured at 75° C. in modified Medium 516, as previously described (Ref #27), with the addition of 5 g/L MOPS. Cellic Ctec2 and Htec2 was used at 4.5 mg and 0.5 mg per gram solid, respectively, unless otherwise noted and incubated with or without D5a yeast at either 37° C. or 50° C. in KN medium as described previously (Ref #45). *C. thermocellum* cellulases were purified from cell-free broth harvested during stationary phase from a pH controlled reactor (Sartorius A+, Bohemia, N.Y.) with initial substrate concentration of 5 g/L Avicel PH-105 (FMC BioPolymer, Philadelphia, Pa.) using the optimized affinity digestion method as described previously (Ref #46). Alternatively, cell-free broth was concentrated in a Biomax tangential flow filter with a NMWL of 10 kDa (Millipore, Billerica, Mass.) and dialyzed in water overnight at 4° C. (Spectra/Por 6-8 kDa MWCO, Rancho Dominguez, Calif.). Residual solids were collected from serum bottles (50 ml working volume) washed and centrifuged twice at 3000×g for 10 min before drying at 60° C. overnight and weighing.

Substrates.

Switchgrass (*Panicum virgatum*, Cave in Rock) was harvested either in June 2012 (mid-season) or April 2013 (senescent) at Rock Springs Research Farm (Spring Mills, Pa.). Due to limited quantities of the senescent Cave in Rock harvest, further studies were conducted with switchgrass (*Panicum virgatum*, Alamo) harvested at University of Tennessee in October 2013. *Populus tremuloides* was harvested as described previously (Ref #47). Feedstocks were washed as previously described (Ref #48) to remove soluble sugars, dried, and milled in either a ED-5 Wiley Mill (0.5-6 mm screens, Thomas Scientific, Swedesboro, N.J.) or ZM200 centrifugal milling machine (0.2 screen, Retsch, Haan, Germany). Unless otherwise noted, substrate was loaded based on equal glucan content (5 g/L) and milled to pass through a 4 mm (switchgrass) or 0.5 mm (*Populus*) sieve. These were chosen as the largest particles sizes which reliably gave solubilization above that for uninoculated controls.

Quantification of Solubilization.

Cell free supernatants were analyzed by HPLC (Waters, Milford Mass.) with an eluent of 5-mM sulfuric acid on an Aminex HPX-87H column (Bio-Rad, Hercules Calif.) and detection by refractive index. Polymeric sugars were analyzed after acid hydrolysis as described previously (Ref #5) and detected as monomers by HPLC and corrected for sugar degradation. Feedstock and residual substrate composition was determined by quantitative saccharification as described by Saeman (Ref #49) and adapted by Sluiter (Ref #50), except the protocol was scaled down to use 0.1 g dry sample, 1 ml 72% sulfuric acid, and 28 ml water. Hydrolyzed sugars were quantified by HPLC and corrected for sugar degradation. Percent solubilization was calculated based on the following equation (for glucan solubilization), $$\% \text{ glucan solubilization} = \frac{\text{initial } g \text{ glucan} - \text{final } g \text{ glucan}}{\text{initial } g \text{ glucan}} * 100$$

Cotreatment.

To mimic one potential configuration for mechanical augmentation (cotreatment), solids (~25 g wet) were ball milled in batches for 5 min (SFM-3, MTI Corporation, Richmond, Calif. with 15 11 mm steel balls) either before or after one 5-day fermentation of senescent switchgrass (Alamo) in a 2 L pH controlled reactor (Sartorius A+). Residual solids were washed and centrifuged twice at 14,300×g for 15 min and triplicate samples (unmilled or milled) were taken and dried to determine moisture content. A second 5-day fermentation was started with carbohydrate loading identical to that at the end of the first fermentation and residuals were collected as described above and stored at 4 C until further analysis. Particle size distribution was determined with a Malvern Mastersizer Hydro 2000G (Worcestershire, UK). Optical properties of wood flour (refractive index of 1.53, absorption of 0.1) and distilled water (refractive index of 1.33) were used for the sample and dispersant, respectively.

Sample Processing for Microscopy. Switchgrass samples were processed using microwave processing as described previously (Ref #51). Briefly, samples were fixed 2×6 min (with variable power) in 2.5% (v/v) gluteraldehyde buffered in 0.1 M sodium cacodylate buffer (EMS, Hatfield, PS) under vacuum. The samples were dehydrated by treating with increasing concentrations of ethanol and heating in a Pelco microwave oven for 1 min at each dilution [i.e., 15%, 30%, 60%, 90% (v/v), and 3×100% ethanol]. After dehydration, the samples were infiltrated with LR White resin (EMS, Hatfield, Pa.) by incubating at room temperature for several hours to overnight in increasing concentrations of resin [15%, 30%, 60%, 90% (v/v), 3×100% resin, diluted in ethanol]. The samples were transferred to capsules and the resin polymerized by heating to 60° C. overnight.

Confocal Scanning Laser Microscopy (CSLM).

Semi-thin sectioned samples were positioned on glass microscope slides and stained with 0.1% acriflavine in water. Images were captured using a 60×1.4NA Plan Apo lenses on a Nikon C1 Plus microscope (Nikon, Tokyo, Japan), equipped with the Nikon C1 confocal system using the Argon tunable laser at 488 nm, and operated via Nikon's EZ-C1 software.

Transmission Electron Microscopy (TEM).

LR White embedded samples were sectioned to ~60 nm with a Diatome diamond knife on a Leica EM UTC ultramicrotome (Leica, Wetzlar, Germany). Sections were collected on 0.5% (v/v) Formvar coated slot grids (SPI Supplies, West Chester, Pa.). All grids were post-stained for 4 min. with 2% (w/v) aqueous uranyl acetate and 2 min. with Reynolds lead citrate. Images were taken with a 4 megapixel Gatan UltraScan 1000 camera (Gatan, Pleasanton, Calif.) on a FEI Tecnai G2 20 Twin 200 kV LaB6 TEM (FEI, Hilsboro, Oreg.).

Example 9

Cotreatment-Enhanced *C. thermocellum* Fermentation

Experiments were performed to investigate cotreatment-enhanced fermentation of lignocellulose by defined microbial cultures. For anaerobic digestion, no reports of cotreatment without reinoculation have been published.

Figure 16:
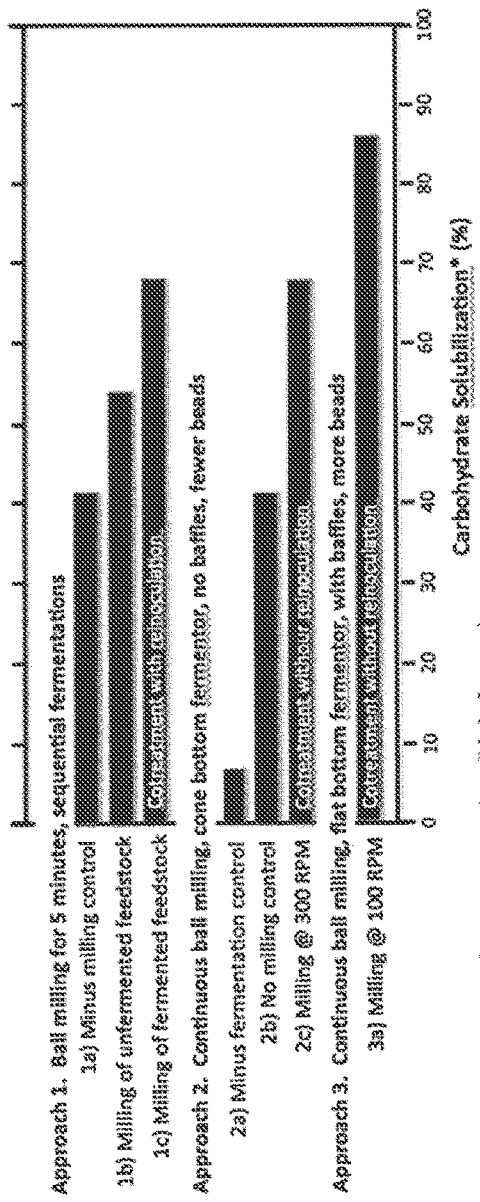
FIG. 16 shows results from fermentation of senescent switchgrass by *C. thermocellum* under different co-treatment schemes.

Cotreatment-enhanced fermentation was investigated for senescent (October harvest) switchgrass by *C. thermocellum* via three approaches: 1) milling between successive fermentations with reinoculation, 2) fermentation with continuous in-situ ball milling in a cone-bottom fermentor with the static height of the bead bed about ⅓ of the liquid height in the reactor and no internal baffles, and 3) fermentation in a flat-bottom fermentor with the static height of the bead bed about 80% of the liquid height (FIG. 16).

For work with approach 1), senescent switchgrass was fermented in pH controlled bioreactors in two 5-day stages. In the first fermentation stage, solids were either milled or not milled for 5 minutes in a dedicated vibratory ball mill at 13 wt. % solids and fermented for 5 days. Residual solids were recovered and washed, milled or not milled as before, resuspended, autoclaved, inoculated and incubated for 5 days.

Data for fermentation of senescent switchgrass by *C. thermocellum* with and without cotreatment were compared. Milling of partially-fermented solids increased total solubilization from 41% to 68% for both approach 1 and approach 2. Enhancement of solubilization was about twice as effective when milling was applied to partially fermented solids as compared to milling applied prior to fermentation. Total carbohydrate solubilization of 86% was achieved in approach 3.

Figure 17:
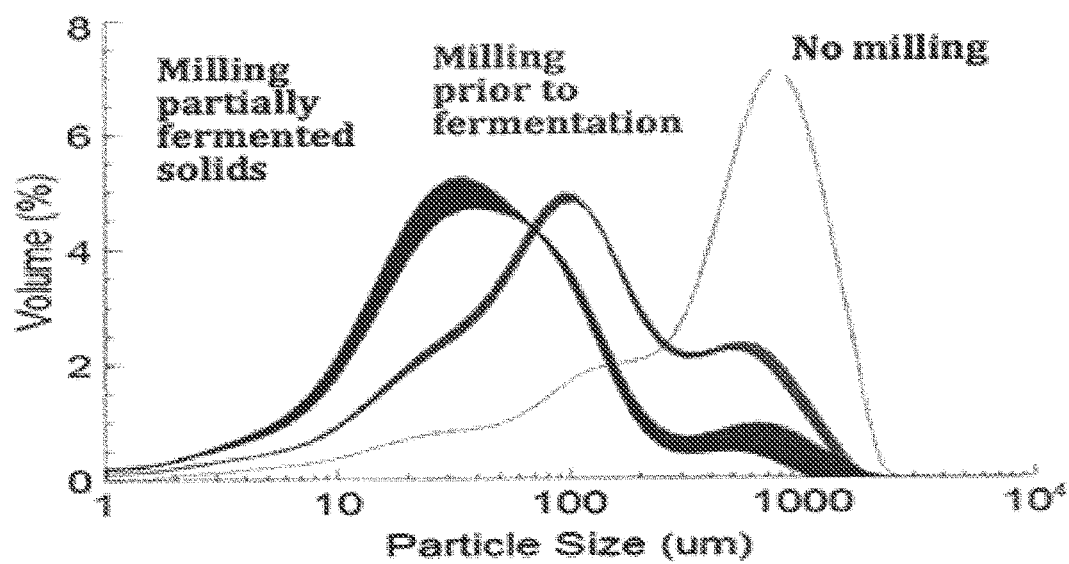
FIG. 17 shows particle size distribution for the tests performed in FIG. 16.

FIG. 17 presents particle size distribution data for conditions 1a), 1b), and 1c) in the experiment depicted in FIG. 16. Consistent with solubilization results, particle size is reduced more effectively by milling partially-fermented solids compared to milling before fermentation, indicating that the mechanical strength of the particles is weakened by fermentation.

Figure 18:
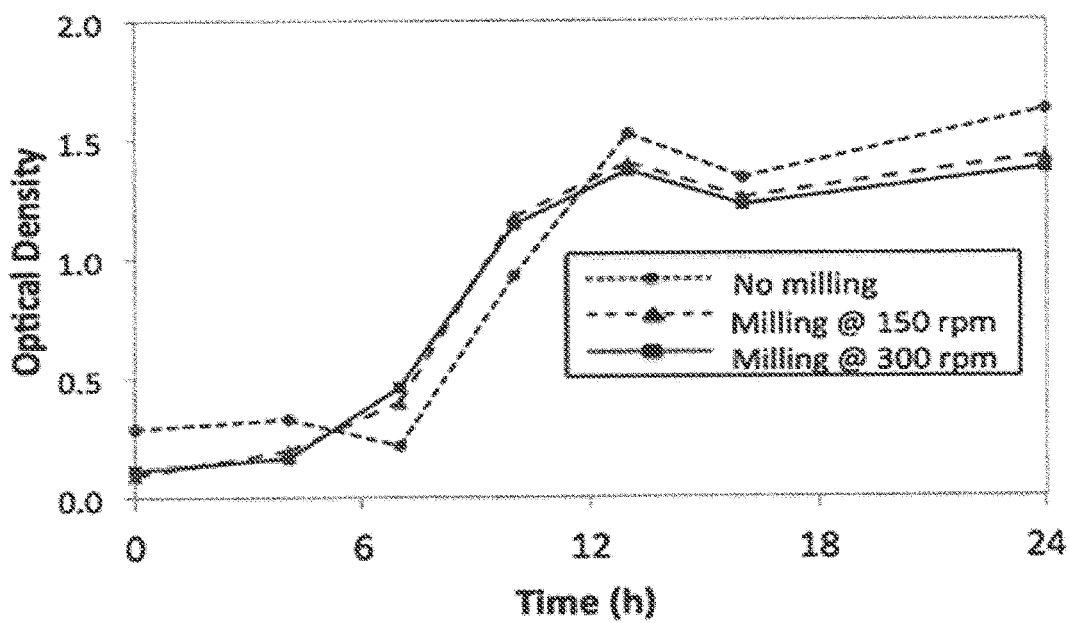
FIG. 18 shows results of fermentation with or without milling.

FIG. 18 presents data for fermentation of cellobiose by *C. thermocellum* with or without continuous milling in the reactor used for cotreatment approach 2. It may be observed that milling at an intensity sufficient to substantially increase solubilization has no significant impact on fermentation dynamics.

By contrast, in similar experiments with glucose fermentation by yeast, yeast is devastated under similar conditions. These data are the first report of a) carbohydrate solubilization comparable to thermochemical pretreatment via cotreatment-enhanced fermentation (FIG. 16), and b) microbial activity maintained in the presence of mechanical feedstock disruption at intensities sufficient to enhance lignocellulose solubilization (FIG. 17).

The contents of all cited references (including literature references, patents, patent applications, and websites) that may be cited throughout this application or listed below are hereby expressly incorporated by reference in their entirety for any purpose into the present disclosure. The disclosure may employ, unless otherwise indicated, conventional techniques of microbiology, molecular biology and cell biology, which are well known in the art.

The disclosed methods and systems may be modified without departing from the scope hereof. It should be noted that the matter contained in the above description or shown in the accompanying drawings should be interpreted as illustrative and not in a limiting sense.

LIST OF REFERENCES

The following references, patents and publication of patent applications are either cited in this disclosure or are of relevance to the present disclosure. All documents listed below, along with other papers, patents and publication of patent applications cited throughout this disclosures, are hereby incorporated by reference as if the full contents are reproduced herein.

1. E. T. Reese, *Biotechnol Bioeng*, 1976, 9-20.
2. D. Sternberg, *Biotechnol Bioeng Symp*, 1976, 35-53.
3. D. Martinez, R. M. Berka, B. Henrissat, M. Saloheimo, M. Arvas, S. E. Baker, J. Chapman, O. Chertkov, P. M. Coutinho, D. Cullen, E. G. J. Danchin, I. V. Grigoriev, P. Harris, M. Jackson, C. P. Kubicek, C. S. Han, I. Ho, L. F. Larrondo, A. L. de Leon, J. K. Magnuson, S. Merino, M. Misra, B. Nelson, N. Putnam, B. Robbertse, A. A. Salamov, M. Schmoll, A. Terry, N. Thayer, A. Westerholm-Parvinen, C. L. Schoch, J. Yao, R. Barbote, M. A. Nelson, C. Detter, D. Bruce, C. R. Kuske, G. Xie, P. Richardson, D. S. Rokhsar, S. M. Lucas, E. M. Rubin, N. Dunn-Coleman, M. Ward and T. S. Brettin, *Nat Biotechnol*, 2008, 26, 553-560.
4. D. Knappert, H. Grethlein and A. Converse, *Biotechnol Bioeng*, 1980, 22, 1449-1463.
5. L. R. Lynd and H. E. Grethlein, *Biotechnol Bioeng*, 1987, 29, 92-100.
6. S. B. McLaughlin and L. A. Kszos, *Biomass Bioenerg*, 2005, 28, 515-535.
7. C. E. Wyman, V. Balan, B. E. Dale, R. T. Elander, M. Falls, B. Hames, M. T. Holtzapple, M. R. Ladisch, Y. Y. Lee, N. Mosier, V. R. Pallapolu, J. Shi, S. R. Thomas and R. E. Warner, *Bioresource Technol*, 2011, 102, 11052-11062.
8. R. T. Elander, B. E. Dale, M. Holtzapple, M. R. Ladisch, Y. Y. Lee, C. Mitchinson, J. N. Saddler and C. E. Wyman, *Cellulose*, 2009, 16, 649-659.
9. L. Johnson, J. H. Harrison, C. Hunt, K. Shinners, C. G. Doggett and D. Sapienza, *J Dairy Sci*, 1999, 82, 2813-2825.
10. R. W. Mellenberger, L. D. Satter, M. A. Millett and A. J. Baker, *J Anim Sci*, 1970, 30, 1005-1011.

11. C. S. W. Reid, A. John, M. J. Ulyatt, G. C. Waghorn and L. P. Milligan, *Ann Rech Vet*, 1979, 10, 205-207.
12. P. M. Kennedy, *Aust J Agr Res*, 1985, 36, 819-828.
13. R. G. Kelsey and F. Shafizadeh, *Biotechnol Bioeng*, 1980, 22, 1025-1036.
14. S. K. Ryu and J. M. Lee, *Biotechnol Bioeng*, 1983, 25, 53-65.
15. M. J. Neilson, R. G. Kelsey and F. Shafizadeh, *Biotechnol Bioeng*, 1982, 24, 293-304.
16. J. M. Lee and J. H. Wolf, *Appl Biochem Biotech*, 1988, 18, 203-215.
17. C. D. Scott and B. H. Davison, U.S. Pat. No. 5,248,484, 1993.
18. U. Mais, A. R. Esteghlalian, J. N. Saddler and S. D. Mansfield, *Appl Biochem Biotech*, 2002, 98, 815-832.
19. J. X. Zhou, D. Chen, Y. H. Zhu, H. D. Liao, L. Yuan, Z. H. Chen and X. M. Liu, *J Chem Technol Blot*, 2010, 85, 85-90.
20. M. H. Sipponen, S. Laakso and S. Baumberger, *Ind Crop Prod*, 2014, 61, 130-136.
21. J. Kopp, J. Muller, N. Dichtl and J. Schwedes, *Water Sci Technol*, 1997, 36, 129-136.
22. C. E. Wyman, B. E. Dale, R. T. Elander, M. Holtzapple, M. R. Ladisch, Y. Y. Lee, C. Mitchinson and J. N. Saddler, *Biotechnol Progr*, 2009, 25, 333-339.
23. T. K. Ng and J. G. Zeikus, *Appl Environ Microb*, 1981, 42, 231-240.
24. E. A. Johnson, M. Sakajoh, G. Halliwell, A. Madia and A. L. Demain, *Appl Environ Microb*, 1982, 43, 1125-1132.
25. R. Waeonukul, A. Kosugi, C. Tachaapaikoon, P. Pason, K. Ratanakhanokchai, P. Prawitwong, L. Deng, M. Saito and Y. Mori, *Bioresource Technol*, 2012, 107, 352-357.
26. S. Kanafusa-Shinkai, J. Wakayama, K. Tsukamoto, N. Hayashi, Y. Miyazaki, H. Ohmori, K. Tajima and H. Yokoyama, *J Biosci Bioeng*, 2013, 115, 64-70.
27. S. J. Yang, I. Kataeva, S. D. Hamilton-Brehm, N. L. Engle, T. J. Tschaplinski, C. Doeppke, M. Davis, J. Westpheling and M. W. W. Adams, *Appl Environ Microb*, 2009, 75, 4762-4769.
28. I. Kataeva, M. B. Foston, S. J. Yang, S. Pattathil, A. K. Biswal, F. L. Poole, M. Basen, A. M. Rhaesa, T. P. Thomas, P. Azadi, V. Olman, T. D. Saffold, K. E. Mohler, D. L. Lewis, C. Doeppke, Y. N. Zeng, T. J. Tschaplinski, W. S. York, M. Davis, D. Mohnen, Y. Xu, A. J. Ragauskas, S. Y. Ding, R. M. Kelly, M. G. Hahn and M. W. W. Adams, *Energ Environ Sci*, 2013, 6, 2186-2195.
29. Y. P. Lu, Y. H. P. Zhang and L. R. Lynd, *P Natl Acad Sci USA*, 2006, 103, 16165-16169.
30. E. T. Reese, *Appl Microbiol*, 1956, 4, 39-45.
31. K. L. Yee, M. Rodriguez, T. J. Tschaplinski, N. L. Engle, M. Z. Martin, C. X. Fu, Z. Y. Wang, S. D. Hamilton-Brehm and J. R. Mielenz, *Biotechnol Biofuels*, 2012, 5.
32. X. Shao, K. DiMarco, T. L. Richard and L. R. Lynd, *Biotechnol Biofuels*, 2015, 8, 35.
33. X. J. Shao, M. J. Jin, A. Guseva, C. G. Liu, V. Balan, D. Hogsett, B. E. Dale and L. Lynd, *Bioresource Technol*, 2011, 102, 8040-8045.
34. J. A. Izquierdo, S. Pattathil, A. Guseva, M. G. Hahn and L. R. Lynd, *Biotechnol Biofuels*, 2014, 7, 136.
35. L. R. Lynd, P. J. Weimer, W. H. van Zyl and I. S. Pretorius, *Microbiol Mol Biol R*, 2002, 66, 506-577.
36. M. G. Resch, B. S. Donohoe, J. O. Baker, S. R. Decker, E. A. Bayer, G. T. Beckham and M. E. Himmel, *Energ Environ Sci*, 2013, 6, 1858-1867.
37. S. E. Blumer-Schuette, S. D. Brown, K. B. Sander, E. A. Bayer, I. Kataeva, J. V. Zurawski, J. M. Conway, M. W. W. Adams and R. M. Kelly, *Fems Microbiol Rev*, 2014, 38, 393-448.
38. P. J. Weimer, J. B. Russell and R. E. Muck, *Bioresource Technol*, 2009, 100, 5323-5331.
39. M. R. Zakaria, S. Hirata and M. A. Hassan, *Bioresource Technol*, 2014, 169, 236-243.
40. G. E. Maciel, W. L. Kolodziejski, M. S. Bertran and B. E. Dale, *Macromolecules*, 1982, 15, 686-687.
41. A. Hideno, H. Inoue, K. Tsukahara, S. Fujimoto, T. Minowa, S. Inoue, T. Endo and S. Sawayama, *Bioresource Technol*, 2009, 100, 2706-2711.
42. P. T. Reed, J. A. Izquierdo and L. R. Lynd, *Bioresource Technol*, 2014, 155, 50-56.
43. E. K. Holwerda, K. D. Hirst and L. R. Lynd, *J Ind Microbiol Biot*, 2012, 39, 943-947.
44. E. Guedon, M. Desvaux, S. Payot and H. Petitdemange, *Microbiology*, 1999, 145 (Pt 8), 1831-1838.
45. K. L. Kadam and M. M. Newman, *Appl Microbiol Biot*, 1997, 47, 625-629.
46. L. A. St Brice, X. J. Shao, J. A. Izquierdo and L. R. Lynd, *Prep Biochem Biotech*, 2014, 44, 206-216.
47. V. Archambault-Leger, X. J. Shao and L. R. Lynd, *Biotechnol Biofuels*, 2012, 5.
48. R. J. Garlock, V. Balan, B. E. Dale, V. R. Pallapolu, Y. Y. Lee, Y. Kim, N. S. Mosier, M. R. Ladisch, M. T. Holtzapple, M. Falls, R. Sierra-Ramirez, J. Shi, M. A. Ebrik, T. Redmond, B. Yang, C. E. Wyman, B. S. Donohoe, T. B. Vinzant, R. T. Elander, B. Hames, S. Thomas and R. E. Warner, *Bioresource Technol*, 2011, 102, 11063-11071.
49. J. F. Saeman, J. L. Bubl and E. E. Harris, *Industrial and Engineering Chemistry-Analytical Edition*, 1945, 17, 35-37.
50. A. Sluiter, B. Hames, R. Ruiz, C. Scarlata, J. Sluiter, D. Templeton and D. Crocker, 2008, NREL/TP-510-42618.
51. B. S. Donohoe, P. N. Ciesielski and T. B. Vinzant, *Methods Mol Biol*, 2012, 908, 31-47.
52. X. J. Shao, M. J. Jin, A. Guseva, C. G. Liu, V. Balan, D. Hogsett, B. E. Dale and L. Lynd, *Bioresource Technol*, 2011, 102, 8040-8045.
53. S. J. Yang, I. Kataeva, S. D. Hamilton-Brehm, N. L. Engle, T. J. Tschaplinski, C. Doeppke, M. Davis, J. Westpheling and M. W. W. Adams, *Appl Environ Microb*, 2009, 75, 4762-4769.
54. I. Kataeva, M. B. Foston, S. J. Yang, S. Pattathil, A. K. Biswal, F. L. Poole, M. Basen, A. M. Rhaesa, T. P. Thomas, P. Azadi, V. Olman, T. D. Saffold, K. E. Mohler, D. L. Lewis, C. Doeppke, Y. N. Zeng, T. J. Tschaplinski, W. S. York, M. Davis, D. Mohnen, Y. Xu, A. J. Ragauskas, S. Y. Ding, R. M. Kelly, M. G. Hahn and M. W. W. Adams, *Energ Environ Sci*, 2013, 6, 2186-2195.
55. J. A. Izquierdo, S. Pattathil, A. Guseva, M. G. Hahn and L. R. Lynd, *Biotechnol Biofuels*, 2014, 7, 136.
56. M. Desvaux, E. Guedon and H. Petitdemange, *Appl Environ Microbiol*, 2000, 66, 2461-2470.
57. J. D. DeMartini, S. Pattathil, U. Avci, K. Szekalski, K. Mazumder, M. G. Hahn and C. E. Wyman, *Energ Environ Sci*, 2011, 4, 4332-4339.
58. S. Pattathil, U. Avci, J. S. Miller and M. G. Hahn, *Methods Mol Biol*, 2012, 908, 61-72.
59. S. Pattathil, U. Avci, D. Baldwin, A. G. Swennes, J. A. McGill, Z. Popper, T. Bootten, A. Albert, R. H. Davis, C. Chennareddy, R. H. Dong, B. O'Shea, R. Rossi, C. Leoff, G. Freshour, R. Narra, M. O'Neil, W. S. York and M. G. Hahn, *Plant Physiol*, 2010, 153, 514-525.

60. M. F. Davis, H. A. Schroeder and G. E. Maciel, *Holzforschung*, 1994, 48, 186-192.
61. C. I. Ishizawa, M. F. Davis, D. F. Schell and D. K. Johnson, *J Agr Food Chem*, 2007, 55, 2575-2581.

What is claimed is:

1. A method for converting biomass into ethanol or other products, said method comprising, in sequential order:
    a) adding said biomass and at least one microorganism to a reactor to form a suspension comprising said biomass and said at least one microorganism,
    b) fermenting said biomass with the at least one microorganism to form a first fermented product comprising fermented biomass and the at least one microorganism, which is a lignocellulosic particle-containing slurry in the reactor,
    c) mechanically disrupting said first fermented product of step (b), wherein the mechanically disrupting comprises mechanical milling,
    d) fermenting the mechanically disrupted product of step (c) in the reactor of step (b),
    wherein said steps (b)-(d) are repeated N times before obtaining said ethanol or other products, N being an integer equal to or greater than 1.

2. The method of claim 1, wherein no reinoculation of said at least one microorganism is included.

3. The method of claim 1, wherein said reactor is operated in batch or continuous mode.

4. The method of claim 1, wherein the mechanically disrupting is performed with a disrupting device external to the reactor, wherein the method comprises a step of withdrawing the lignocellulosic particle-containing slurry from the reactor.

5. The method of claim 1, wherein said reactor is a closed reactor.

6. The method of claim 1, wherein more than 60% of sugar in said biomass is solubilized after said biomass is fermented for 5-day in each of steps (b) and (d).

7. The method of claim 1, wherein said at least one microorganism is at least one member selected from the group consisting of *Clostridium thermocellum, Clostridium claraflavum, Clostridium cellulolyticum, Caldicellusiruptor bescii, Thermoanaerobacterium saccharolyticum, Thermoanaerobacterium thermosaccharolyticum* and combination thereof.

8. The method of claim 1, wherein the method does not utilize yeast or purified cellulase.

9. The method of claim 1, wherein no chemical treatment is applied to said biomass prior to step (b) to increase the accessibility of said biomass to said at least one microorganism.

* * * * *